(12) United States Patent
Waggoner

(10) Patent No.: US 7,008,798 B2
(45) Date of Patent: *Mar. 7, 2006

(54) CYANINE DYES AS LABELING REAGENTS FOR DETECTION OF BIOLOGICAL AND OTHER MATERIALS BY LUMINESCENCE METHODS

(75) Inventor: Alan S. Waggoner, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 55 days.

This patent is subject to a terminal disclaimer.

(21) Appl. No.: 10/103,116

(22) Filed: Mar. 22, 2002

(65) Prior Publication Data

US 2002/0146736 A1 Oct. 10, 2002

Related U.S. Application Data

(60) Division of application No. 09/740,486, filed on Dec. 19, 2000, which is a continuation of application No. 08/745,712, filed on Nov. 12, 1996, now Pat. No. 6,225,050, which is a continuation-in-part of application No. 07/831,759, filed on Sep. 22, 1992, now Pat. No. 5,627,027, which is a continuation of application No. 06/854,347, filed on Apr. 18, 1986, now abandoned.

(51) Int. Cl.
*G01N 33/566* (2006.01)

(52) U.S. Cl. .............. 436/501; 514/222.2; 514/224.2; 514/183; 436/111; 544/113; 544/83; 544/212; 548/150

(58) Field of Classification Search ............... 435/6, 435/7.1; 436/86, 11, 501, 800, 172, 111; 544/212, 113, 83, 465, 469; 548/465, 469, 548/150, 156; 514/183, 222.2, 224.2
See application file for complete search history.

(56) References Cited

U.S. PATENT DOCUMENTS

| 279,524 A | 6/1883 | Beaty ..................... 607/145 |
| 484,522 A | 10/1892 | McBride |
| 600,290 A | 3/1898 | Muir |
| 1,967,927 A | 7/1934 | Deustch ..................... 604/20 |
| 2,047,308 A | 7/1936 | Chapman ................... 128/799 |
| 2,126,070 A | 8/1938 | Wappler |
| 2,834,344 A | 5/1958 | Kanai |
| 3,019,787 A | 2/1962 | Simmons |
| 3,048,170 A | 8/1962 | Lemos |
| 3,107,672 A | 10/1963 | Hofmann |
| 3,148,187 A | 9/1964 | Heseltine ................. 260/240.4 |
| 3,163,166 A | 12/1964 | Brant et al. |
| 3,298,368 A | 1/1967 | Charos ...................... 128/260 |
| 3,423,207 A | 1/1969 | Heseltine et al. ............. 96/84 |
| 3,481,927 A | 12/1969 | Heseltine et al. ........ 260/240.9 |
| 3,520,297 A | 7/1970 | Bechtold |
| 3,645,260 A | 2/1972 | Cinotti et al. |
| 3,716,054 A | 2/1973 | Porter et al. |
| 3,831,598 A | 8/1974 | Tice |
| 3,848,600 A | 11/1974 | Patrick, Jr. et al. ......... 128/783 |
| 4,040,825 A | 8/1977 | Steiger et al. ................ 430/95 |
| 4,094,745 A | 6/1978 | Scholefeld ................... 435/39 |
| 4,116,238 A | 9/1978 | Pettijohn ................. 128/172.1 |
| 4,138,551 A | 2/1979 | Steiger et al. ............. 542/435 |
| 4,166,105 A | 8/1979 | Hirschfeld .................. 436/536 |
| 4,211,222 A | 7/1980 | Tapper ....................... 128/803 |
| 4,256,834 A | 3/1981 | Zuk et al. .................. 435/7.72 |
| 4,268,622 A | 5/1981 | Adachi et al. .............. 430/513 |
| 4,292,968 A | 10/1981 | Ellis ...................... 128/207.21 |
| 4,301,794 A | 11/1981 | Tapper ........................ 604/20 |
| 4,325,367 A | 4/1982 | Tapper |
| 4,337,063 A | 6/1982 | Mihara et al. .............. 436/536 |
| 4,337,065 A | 6/1982 | Hiratsuka et al. ........... 436/543 |
| 4,343,782 A | 8/1982 | Shapiro ..................... 435/7.2 |
| 4,383,529 A | 5/1983 | Webster |
| 4,393,884 A | 7/1983 | Jacobs ........................ 131/273 |
| 4,404,289 A | 9/1983 | Masuda et al. ............. 436/538 |
| 4,405,711 A | 9/1983 | Masuda et al. ................ 435/4 |
| 4,406,658 A | 9/1983 | Lattin et al. .................. 604/20 |
| 4,414,325 A | 11/1983 | Masuda et al. .............. 435/7.4 |

(Continued)

FOREIGN PATENT DOCUMENTS

AT      OE 0232642      3/1964      ................... 604/20

(Continued)

OTHER PUBLICATIONS

M.J. Anderson et al., "Fluorescent Staining of Acetylcholine Receptors in Vertebrate Skeletal Muscle", J. Physiol., vol. 237, pp. 385-400 (1974).

(Continued)

*Primary Examiner*—Padmashri Ponnaluri
(74) *Attorney, Agent, or Firm*—Nixon & Vanderhye P.C.

(57) ABSTRACT

The present invention pertains to luminescent dyes and methods for covalently attaching the dyes to a component or mixture of components so that the components may be detected and/or quantified by luminescence detection methods. The dyes are cyanine and cyanine-type dyes that contain or are derivatized to contain a reactive group. The reactive group is covalently reactive with amine, hydroxy and/or sulfhydryl groups on the component so that the dye can be covalently bound to the component. In addition, the dyes are preferably soluble in aqueous or other medium in which the component is contained. The components to be labeled can be either biological materials, such as antibodies, antigens, peptides, nucleotides, hormones, drugs, or non-biological materials, such as polymers, glass, or other surfaces. Any luminescent or light absorbing detecting step can be employed in the method of the invention.

2 Claims, 5 Drawing Sheets

U.S. PATENT DOCUMENTS

| | | | |
|---|---|---|---|
| 4,416,274 A | 11/1983 | Jacobsen et al. ............ 128/803 |
| 4,429,050 A | 1/1984 | Yasuda et al. .............. 436/538 |
| 4,429,703 A | 2/1984 | Haber ........................ 131/273 |
| 4,474,570 A | 10/1984 | Ariura et al. ................. 604/20 |
| 4,510,939 A | 4/1985 | Brenman et al. ........... 128/639 |
| 4,542,104 A | 9/1985 | Stryer et al. ................ 436/536 |
| 4,584,277 A | 4/1986 | Ullman ...................... 435/7.25 |
| 4,639,244 A | 1/1987 | Rizk et al. |
| 4,655,229 A | 4/1987 | Sensabaugh, Jr. et al. .. 131/273 |
| 4,665,921 A | 5/1987 | Teranishi et al. |
| 4,689,039 A | 8/1987 | Masaki |
| 4,702,732 A | 10/1987 | Powers et al. |
| 4,708,716 A | 11/1987 | Sibalis ........................ 604/20 |
| 4,735,217 A | 4/1988 | Gerth et al. ................ 131/273 |
| 4,747,819 A | 5/1988 | Phipps et al. |
| 4,748,129 A | 5/1988 | Chang et al. .............. 435/7.25 |
| 4,756,318 A | 7/1988 | Clearman et al. ........... 131/359 |
| 4,763,660 A | 8/1988 | Kroll et al. ................. 128/798 |
| 4,764,164 A | 8/1988 | Sasaki ........................ 604/20 |
| 4,767,402 A | 8/1988 | Kost et al. |
| 4,770,992 A | 9/1988 | Van de Engh et al. ......... 435/6 |
| 4,771,796 A | 9/1988 | Myer ........................ 131/273 |
| 4,776,353 A | 10/1988 | Lilja et al. .................. 131/297 |
| 4,786,278 A | 11/1988 | Masaki ........................ 604/20 |
| 4,787,888 A | 11/1988 | Fox |
| 4,793,366 A | 12/1988 | Hill ............................ 131/273 |
| 4,800,903 A | 1/1989 | Ray et al. .................... 131/273 |
| 4,808,152 A | 2/1989 | Sibalis ........................ 604/20 |
| 4,813,437 A | 3/1989 | Ray ............................ 131/273 |
| 4,820,263 A | 4/1989 | Spevak et al. ................ 604/20 |
| 4,820,630 A | 4/1989 | Taub ............................ 435/5 |
| 4,821,740 A | 4/1989 | Tachibana et al. ............ 604/20 |
| 4,829,070 A | 5/1989 | Bodor ........................ 514/307 |
| 4,838,273 A | 6/1989 | Cartmell ..................... 600/392 |
| 4,865,582 A | 9/1989 | Sibalis ........................ 604/20 |
| 4,907,606 A | 3/1990 | Lilja et al. .................. 131/273 |
| 4,913,148 A | 4/1990 | Diethelm |
| 4,917,119 A | 4/1990 | Potter et al. ................ 131/273 |
| 4,919,648 A | 4/1990 | Sibalis ........................ 604/20 |
| 4,922,901 A | 5/1990 | Brooks et al. ......... 128/203.26 |
| 4,931,046 A | 6/1990 | Newman ..................... 604/20 |
| 4,942,883 A | 7/1990 | Newman ..................... 604/20 |
| 4,950,229 A | 8/1990 | Sage, Jr. ...................... 604/20 |
| 4,953,565 A | 9/1990 | Tachibana et al. ............ 604/20 |
| 4,957,480 A | 9/1990 | Morenings |
| 4,979,938 A | 12/1990 | Stephen et al. |
| 4,997,418 A | 3/1991 | DeMartini |
| 5,002,527 A | 3/1991 | Reller et al. |
| 5,006,108 A | 4/1991 | LaPrade ..................... 604/20 |
| 5,019,034 A | 5/1991 | Weaver et al. ................ 604/20 |
| 5,037,381 A | 8/1991 | Bock et al. |
| 5,042,975 A | 8/1991 | Chien et al. |
| 5,047,007 A | 9/1991 | McNichols et al. ........... 604/20 |
| 5,053,001 A | 10/1991 | Reller et al. .................. 604/20 |
| 5,060,671 A | 10/1991 | Counts et al. .............. 131/329 |
| 5,090,402 A | 2/1992 | Bazin et al. |
| 5,106,990 A | 4/1992 | Ohno et al. ................. 584/427 |
| 5,115,805 A | 5/1992 | Bommannan et al. |
| 5,133,352 A | 7/1992 | Lathrop et al. |
| 5,135,478 A | 8/1992 | Sibalis |
| 5,135,479 A | 8/1992 | Sibalis et al. .................. 604/20 |
| 5,147,291 A | 9/1992 | Cukier ........................ 604/22 |
| 5,160,316 A | 11/1992 | Henley ........................ 604/20 |
| 5,162,042 A | 11/1992 | Gyory et al. |
| 5,167,242 A | 12/1992 | Turner et al. ................ 131/273 |
| 5,169,384 A | 12/1992 | Bosniak et al. |
| 5,171,215 A | 12/1992 | Flanagan ..................... 604/20 |
| 5,203,768 A | 4/1993 | Haak et al. |
| 5,250,022 A | 10/1993 | Chien et al. |
| 5,254,081 A | 10/1993 | Maurer et al. ................ 604/20 |
| 5,268,486 A | 12/1993 | Waggoner et al. .......... 548/427 |
| 5,279,543 A | 1/1994 | Glikfeld et al. |
| 5,284,471 A | 2/1994 | Sage, Jr. |
| 5,298,017 A | 3/1994 | Theeuwes et al. |
| 5,310,404 A | 5/1994 | Gyory et al. |
| 5,312,326 A | 5/1994 | Myers et al. |
| 5,314,502 A | 5/1994 | McNichols et al. |
| 5,331,979 A | 7/1994 | Henley |
| 5,354,321 A | 10/1994 | Berger |
| 5,360,440 A | 11/1994 | Andersen |
| 5,362,307 A | 11/1994 | Guy et al. |
| 5,362,308 A | 11/1994 | Chien et al. |
| 5,374,241 A | 12/1994 | Lloyd et al. |
| 5,374,242 A | 12/1994 | Haak et al. |
| 5,376,107 A | 12/1994 | Inagi et al. |
| 5,391,195 A | 2/1995 | Van Groningen |
| 5,395,310 A | 3/1995 | Untereker et al. |
| 5,413,590 A | 5/1995 | Williamson |
| 5,415,629 A | 5/1995 | Henley |
| 5,421,816 A | 6/1995 | Lipkovker |
| 5,441,936 A | 8/1995 | Houghten et al. |
| 5,443,441 A | 8/1995 | De Claviere |
| 5,458,569 A | 10/1995 | Kirk, III et al. .............. 604/20 |
| 5,464,387 A | 11/1995 | Haak et al. |
| 5,466,217 A | 11/1995 | Myers et al. |
| 5,470,349 A | 11/1995 | Kleditsch et al. |
| 5,494,679 A | 2/1996 | Sage, Jr. et al. |
| 5,501,705 A | 3/1996 | Fakhri |
| 5,514,167 A | 5/1996 | Smith et al. |
| 5,538,503 A | 7/1996 | Henley |
| 5,540,669 A | 7/1996 | Sage, Jr. et al. .............. 604/20 |
| 5,551,953 A | 9/1996 | Lattin et al. |
| 5,556,959 A | 9/1996 | Brush et al. |
| 5,558,632 A | 9/1996 | Lloyd et al. |
| 5,562,607 A | 10/1996 | Gyory |
| 5,569,587 A | 10/1996 | Waggoner ...................... 435/6 |
| 5,569,766 A | 10/1996 | Waggoner et al. .......... 548/150 |
| 5,589,563 A | 12/1996 | Ward et al. |
| 5,603,693 A | 2/1997 | Frenkel et al. |
| 5,607,461 A | 3/1997 | Lathrop |
| 5,607,691 A | 3/1997 | Hale et al. |
| 5,618,275 A | 4/1997 | Bock |
| 5,627,027 A | 5/1997 | Waggoner ...................... 435/6 |
| 5,658,247 A | 8/1997 | Henley |
| 5,667,487 A | 9/1997 | Henley |
| 5,668,170 A | 9/1997 | Gyory |
| 5,676,648 A | 10/1997 | Henley |
| 5,678,273 A | 10/1997 | Porcelli |
| 5,688,233 A | 11/1997 | Hofmann et al. |
| 5,697,896 A | 12/1997 | McNichols et al. |
| 5,700,457 A | 12/1997 | Dixon |
| 5,711,761 A | 1/1998 | Untereker et al. |
| 5,713,846 A | 2/1998 | Bernhard et al. |
| 5,722,397 A | 3/1998 | Eppstein |
| 5,725,817 A | 3/1998 | Milder |
| 5,733,255 A | 3/1998 | Dinh et al. |
| 5,755,750 A | 5/1998 | Petruska et al. |
| 5,788,666 A | 8/1998 | Atanasoska |
| 5,794,774 A | 8/1998 | Porcelli |
| 5,795,321 A | 8/1998 | McArthur et al. |
| 5,797,867 A | 8/1998 | Guerrera et al. |
| 5,830,175 A | 11/1998 | Flower |
| 5,840,057 A | 11/1998 | Aloisi |
| 5,846,217 A | 12/1998 | Beck et al. |
| 5,865,786 A | 2/1999 | Sibalis et al. ................. 604/20 |
| 5,879,323 A | 3/1999 | Henley |
| 5,882,676 A | 3/1999 | Lee et al. |
| 5,899,876 A | 5/1999 | Flower ........................ 604/20 |
| 5,908,401 A | 6/1999 | Henley ........................ 604/20 |
| 5,911,319 A | 6/1999 | Porcelli et al. |
| 5,919,155 A | 7/1999 | Lattin et al. .................. 604/20 |
| 5,931,859 A | 8/1999 | Burke |
| 5,935,598 A | 8/1999 | Sage et al. |
| 5,954,684 A | 9/1999 | Flower et al. ................. 604/20 |

| | | | |
|---|---|---|---|
| 5,961,482 A | 10/1999 | Chien et al. | |
| 5,961,483 A | 10/1999 | Sage et al. | |
| 5,968,005 A | 10/1999 | Tu | |
| 5,968,006 A | 10/1999 | Hofmann | |
| 5,983,130 A | 11/1999 | Phipps et al. | |
| 6,004,309 A | 12/1999 | Phipps | |
| 6,004,547 A | 12/1999 | Rowe et al. | |
| 6,006,130 A | 12/1999 | Higo et al. | |
| 6,018,679 A | 1/2000 | Dinh et al. | |
| 6,023,639 A | 2/2000 | Hakky et al. | |
| 6,032,073 A | 2/2000 | Effenhauser | |
| 6,038,485 A | 3/2000 | Axelgaard | |
| 6,041,252 A | 3/2000 | Walker et al. | |
| 6,041,253 A | 3/2000 | Kost et al. | |
| 6,048,545 A | 4/2000 | Keller et al. | |
| 6,048,982 A | 4/2000 | Waggoner | 548/148 |
| 6,057,374 A | 5/2000 | Huntington et al. | |
| 6,101,411 A | 8/2000 | Newsome | |
| 6,148,231 A | 11/2000 | Henley | 604/20 |
| 6,148,232 A | 11/2000 | Avrahami | 604/20 |
| 6,167,302 A | 12/2000 | Millot | |
| 6,225,050 B1 | 5/2001 | Waggoner | 435/6 |
| 6,385,487 B1 | 5/2002 | Henley | 604/20 |

FOREIGN PATENT DOCUMENTS

| | | | |
|---|---|---|---|
| BE | 669003 | 1/1963 | |
| EP | 0230749 | 8/1987 | 604/20 |
| EP | 0309093 A1 | 3/1989 | 604/20 |
| EP | 617979 A1 | 10/1994 | |
| FR | 1445703 | 6/1966 | 604/20 |
| FR | 2 513 129 | 3/1983 | |
| GB | 0299553 | 11/1928 | 604/20 |
| GB | 1529202 | 10/1978 | |
| JP | 1-239548 | 9/1989 | |
| JP | 3-170172 | 7/1991 | |
| JP | 6-122696 | 5/1994 | |
| SU | 654254 | 3/1979 | |
| SU | 931191 | 5/1982 | |
| SU | 1003853 | 3/1983 | |
| WO | 07269 | 12/1986 | 604/20 |
| WO | WO 90/06153 | 6/1990 | |
| WO | 08571 | 8/1990 | 604/20 |
| WO | 03790 | 3/1993 | 604/20 |
| WO | 95/04747 | 2/1995 | |
| WO | WO 95/04747 | 2/1995 | |

OTHER PUBLICATIONS

M.E. Bayer et al., "Fast responses of bacterial membranes to virus adsorption: A fluorescence study", Proc. Natl. Acad. Science USA, vol. 78, No.9, pp. 5618-5622 (1981).

P.K. Bhattacharyya et al., "Fluorescent Labelling of Strychnine: A Novel Approach for Recognition of Strychnine Binding Sites on Neuronal Membrane", Biochemical and Biophysical Research Communications, vol. 101, No. 1, pp. 273-274 (1981).

A.N. De Belder et al., "Preparation and Properties of Fluorescein-Labelled Dextrans", Carbohydrate Research, vol. 30, pp. 375-378, pp. (1973).

P. Brandtzaeq, "Rhodamine Conjugates: Specific and Nonspecific Binding Properties in Immunihistochemistry", Annals New York Academy of Sciences, vol. 254, pp. 35-55 (1975).

B.C.F. Chu et al., "Derivation of Unprotected Polynucleotides", Nucleic Acids Research, vol. 11, No. 18, pp. 6513-6529 (1983).

M. Edidin et al., "Measurements of Membrane Protein Lateral Diffusion in Single Cells", Science, vol. 191, pp. 466-468 (1976).

D.J. Gale et al., "Fibre Reactive Basic Dyes: I-Polymethine Dyes Containing the N-Chloroacetyl Group", J. Soc. Dyers and Colorists, vol. 9, pp. 97-100 (1974).

D.J. Gale et al., "The Amidomethylation and Bromination of Fischer's Base. The Preparation of Some New Polymethine Dyes", Aust. J. Chem., vol. 30, pp. 689-694 (1977).

A.N. Glazer et al., "Phycofluor Probes", Emerging Techniques, TIBS, pp. 423-429 (1984).

H. Haigler et al., "Visualization by Fluorescence of the Binding and Internalization of Epidermal Growth Factor in Human Carcinoma Cells a-431", Proc. Natl. Acad. Sci. USA, vol. 75, No. 7, pp. 3317-3321 (1978).

F.M. Hamer, "The Cyanine Dyes and Related Compounds", Interscience Publishers, pp. 86-350, 398-399, 511-513, 693-694 and 704 (Chapters 4-10) (1964).

R.P. Haugland, "Covalent Fluorescent Probes", Excited States of Biopolymers, Plenum Press, pp. 29-58.

H. Hayatsu, "Reaction of Cytidine with Semicarbazide in the Presence of Bisulfite. A Rapid Modification Specific for Single-Stranded Polynucleotide", Biochemistry, vol. 15, No. 12, pp. 2677-2682 (1976).

F.W. Hoffman, "Styryl Dyes", Chemical Abstracts: 46-Dyes, vol. 65, Cols. 9070, 9071 and 9072 (1966).

Jacobsen et al., "Internatinal Workshop on the Application of Fluorescence Photobleaching Techniques to Problems in Cell Biology", Federation Proceedings, vol. 42, pp. 72-79 (1973).

M.N. Kronick et al., "Immunoassay Techniques with Fluorescent Phycobiliprotein Conjugates", Reprinted from Clinical Chemistry, vol. 29, pp. 1582-1586 (1983).

Biosis Abstract No. 78081829, Latt et al., "New Fluorochromes Compatible with High Wavelength Excitation for Flow Cytometric Analysis of Cellular Nucleic Acids", Cytometry, vol. 5, No. 4, pp. 339-347 (1984).

M.R. Loken et al., "Lymphoin Cell Analysis and Sorting", Flow Cytometry and Sorting, pp. 505, 522-523 (1979).

R.M. McKinney et al., "An Approach to Quantitation in Rhodamine Isothiocyanate Labeling", Annals New York Academy of Sciences, vol. 254, pp. 55-65 (1975).

K.A. Muirhead et al., "Flow Cytometry: Present and Future", Review, Biotechnology, vol. 3, (Apr. 1985).

B.S. Packard et al., "Intracellular Dye Heterogeneity Determined by Fluorescence Lifetimes", Biochimica et Biophysica Acta, vol. 769, pp. 201-208 (1984).

J.S. Ploem, "General Introduction", Fifth International Conference on Immunofluorescence and Related Staining Techniques, Annals of the N.Y. Academy of Sciences, vol. 254, pp. 1-20 (1975).

G. Salama et al., "Sulfhydryl Reagent Dyes Trigger the Rapid Release of $Ca^{2+}$ from Sarcoplasmic Reticulum Vesicles (SR)", Biophysical Journal, vol. 47, p. 456a (1985). (W-Pos 197).

R.D. Spencer et al., "Design, Construction, and Two Applications for an Automated Flow-Cell Polarization Fluorometer with Digital Read Out: Enzyme-Inhibitor (Antitrypsin) Assay and Antigen-Antibody (Insulin—Insulin Antiserum) Assay", Clinical Chem., vol. 19, No. 8, pp. 838-844 (1973).

L.M. Smith et al., "The Synthesis of Oligonucleotides Containing an Aliphatic Amino Group at the 5' Terminus: Synthesis of Fluorescent DNA Primers for use in DNA Sequence Analysis", Nucleic Acids Research, vol. 13, pp. 2399-2407 (1985).

L. Stryer, "Fluorescent Conjugates for Analysis of Molecules and Cells", Biochem. Methods, vol. 59, paragraph 99:154827f, p. 311 (1984).

The Theory of the Photographic Process, Fourth Edition (T.H. James Ed.), Chapter 8: "Sensitizing and Desensitizing Dyes", D.M. Sturmer and D.W. Heseltine, pp. 194-197 (1977).

D.M. Sturmer, "Syntheses and Properties of Cyanine and Related Dyes", Special Topics in Heterocyclic Chemistry, vol. 30, Chapter VIII, pp. 441-587 (1977).

Tadahiro Oonishi et al., "A New Standard Fluorescence Microsphere for Quantitative Flow Cytometry", Journal of Immunological Methods, vol. 84, pp. 143-154 (1985).

K. Venkataraman, The Chemistry of Synthetic Dyes, vol. IV (H. Meier Ed.), Academic Press, New York, pp. 212-213 (1971).

A.S. Waggoner et al., "The Kinetics of Conformational Changes in a Region of the Rhodopsin Molecule Away from the Retinylidene Binding Site", Biophysical Journal, vol. 33, p. 292a (1981). (W-AM-Po13).

Bayer et al "Fast responses of bacterial membranes to virus adsorption: A fluorescence study", Proc. Nat'l Acad. Science, vol. 78, No. 9, pp. 5618-5622 (1981).

Smith et al "The synthesis of oligonucleotides containing an aliphatic amino group at the 5' terminus:synthesis of fluorescent DNA primers for use in DNA sequence analysis", Nucleic Acid Research, pp. 2399-2407.

The Chemistry of Synthetic Dyes, vol. IV (H. Meier Ed.), Academic Press, New York, Chapter V: "Cyanine Dyes", G.E. Ficken (1971), pp. 334-335.

Römpps Chemie-Lexikon, 8$^{th}$ edition, 1987, keyword "Polymethin-Farbstoffe" (polymethine dyes), as well as—for additional opinion reasons—Römpps Chemie-Lexikon, version 2.0, 1999, printout keyword "Polymethin-Farbstoffe" (polymethine dyes).

Larry S. Barak and Watt W. Webb: Fluorescent Low Density Lipoprotein for Observation of Dynamics of Individual Receptor Complexes on Cultured Human Fibroblasts; The Journal of Cell Biology, vol. 90, Sep. 1981, pp. 595-604.

English translation of an Opposition setting out the grounds for an opposition filed against German patent DE 39 43 862 B4 granted Jan. 22, 2004.

Salama et al, "Sulfhydryl Reagent Dyes Trigger the Rapid Release of $Ca^{2+}$ From Sarcoplasmic Reticulum Vesticles (Sr).", Biophysical Journal, Feb., 1985, vol. 47, No. 2, Part 2.

"Iontophoretic Treatment of Oral Herpes," Henley et al.; Laryngoscope, vol. 94, No. 1, pp. 118-121, Jan. 1984.

"Iontophoretic Application of Idoxuridine for Recurrent Herpes Labialis: Report of Preliminary Chemical Trials," Gangarosa et al.; Meth. And Find. Exptl. Clin. Pharmacol. 1(2), pp. 105-109 (1979).

"Iontophoresis of Vidarabine Monophosphate for Herpes Orolabialis," Gangarosa et al.; The Journal of Infectious Diseases, vol. 154, No. 6, pp. 930-934, Dec. 1986.

"The Natural History of Recurrent Herpes Simplex Labialis," Spruance et al.; The New England Journal of Medicine, vol. 297, No. 2, pp. 69-75, Jul. 14, 1977.

"Infection with Herpes-Simplex Viruses 1 and 2," Nahmias et al.; The New England Journal of Medicine, pp. 667-674, Sep. 27, 1973.

"Anesthesia of the Human Tympanic Membrane by Iontophoresis of a Local Anesthetic," Corneau et al.; The Laryngoscope, 88:1978, pp. 277-285.

"Iontophoretic Application of Drugs," Waud, J. Appl. Physiol. 23(1), 1967, pp. 128-130.

"Antibiotic Iontophoresis in the Treatment of Ear Chondritis," LaForest et al., Physical Therapy, vol. 58, No. 1, Jan. 1978, pp. 32-34.

"The Quantity and Distribution of Radiolabeled Dexamethasone Delivered to Tissue by Iontophoresis," Glass et al.; Internatiional Journal of Dermatology, vol. 19, Nov. 1980, pp. 519-525.

"Iontophoretic Application of Antiviral Chemotherapeutic Agents," Hill et al., Annals New York Academy of Sciences, pp. 604-612.

"Ocular Iontophoresis," Hill et al. Paper, Louisiana State University Medical Center, School of Medicine, New Orleans, Louisiana, pp. 331-354.

"Iontophoretic Application of Adenine Arabinoside Monophosphate to Herpes Simplex Virus type 1-Infected Hairless Mouse Skin," Park et al.; Antimicrobial Agents and Chemotherapy, vol. 14, No. 4, Oct. 1978, pp. 605-608.

"Iontophoresis: Applications in Transdermal Medication Delivery," Costello et al.; Physical Therapy, vol. 75, No. 6, pp. 104/554-113/563, Jun. 1995.

Physical Enhancement of Dermatologic Drug Delivery: Iontophoresis and Phonophoresis, Kassan et al., Journal of the American Academy of Dermatology, Apr. 1996, pp. 657-666.

"Iontophoresis and Herpes Labialis," Boxhall et al.; The Medical Journal of Australia, May 26, 1984, pp. 686-687.

"Iontophoresis: A Method of Antibiotic Administration in the Burn Patient," Rapperport et al., Plastic and Reconstructive Surgery, 1965, vol. 36, No. 5, pp. 547-552.

"Iontophoresis for Enhancing Penetration of Dermatologic and Antiviral Drugs," Gangarosa et al., Journal of Dermatology, vol. 22, No. 11, pp. 865-875, Nov. 1995.

"Iontophoretic Treatment of Herpetic Whitlow," Gangarosa et al., Arch. Phys. Med. Rehabil., vol. 70, pp. 336-340Apr. 1989.

"Iontophoretic Application of Antiviral Drugs," Gangarosa et al., Proceedings of an International Symposium held in Tokushima City, Japan, pp. 201-204, Jul. 27-30, 1981.

"Iontophoretic Application of Adenine Arabinoside Monophosphate for the Treatment of Herpes Simplex Virus Type 2 Skin Infections in Hairless Mice," Gangarosa, The Journal of Infectious Diseases, vol. 140, No. 6, pp. 1014, Dec. 1979.

"Effect of Iontophoretic and Topical Application of Antiviral Agents in Treatment of Experimental HSV-1 Keratitis in Rabbits," Kwon et al., Investigative Ophthalmology & Visual Science, vol. 18, No. 9, pp. 984-988, Sep., 1979.

"Acyclovir and Vidarabine Monophosphate: Comparison of Iontophoretic and Intravenous Administration for the Treatment of HSV-1 Stromal Keratitis," Hill et al., The American Journal of Medicine, Acyclovir Symposium, pp. 300-304.

"Thymine Arabinoside (Ara-T) Topical and Iontophoretic Applications for Herpes Simplex Virus Type 1 and Type 2 Skin Infections in Hairless Mice," Hill et al., Meth. And Find. Exptl. Clin. Pharmacol. 6(1), pp. 17-20, 1984.

"Iontophoresis Enhances the Transport of Acyclovir Through Nude Mouse Skin by Electrorepulsion and Electroosmosis," Volpato et al., Pharmaceutical Research, vol. 12, No. 11, pp. 1623-1627, 1995.

"Early Application of Topical 15% Idoxuridine n Dimethyl Sulfoxide Shortens the Course of Herpes Simplex Labialis: A Multicenter Placebo-Controlled Trial," Spruance et al., The Journal of Infectious Diseases, 1990; vol. 161; pp. 191-197.

"Iontophoresis for Surface Local Anesthesia," Gangarosa, JADA, vol. 88, pp. 125-128, Jan. 1974.

"Conductivity of Drugs Used for Iontophoresis," Gangarosa et al., Journal of Pharmaceutical Sciences, vol. 67, No. 10, pp. 1439-1443, Oct., 1978.

"A Pilot Study of Iontophoretic Cisplatin Chemotherapy of Basal and Squamous Cell Carcinomas of the Skin," Chang et al., Arch. Dermatol., vol. 129, pp. 425-427, Apr. 1993.

"How Modern Iontophoresis Can Improve Your Practice," Gangarosa et al., (Quintessence International) Oral Surgery, No. 10, Report 2135, Oct. 1982, pp. 1027-1038.

"Postherpetic Neuralgia," Baron et al., Brain (1993), 116, pp. 1477-1496.

"Iontophoretic Assistance of 5-Iodo-2'-Deoxyuridine Penetration into Neonatal Mouse Skin and Effects of DNA Synthesis," Gangarosa et al., Society for Experimental Biology and Medicine, pp. 439-443, 1977.

"Electrophoretic Evaluation of the Mobility of Drugs Suitable for Iontophoresis," Kamath et al., Meth. Find. Exp. Clin. Pharmacol., 1995, 17(4):pp. 227-232.

"Transdermal Drug Delivery by Passive Diffusion and Iontophoresis: A Review," Singh et al., Medicinal Research Reviews, vol. 13, No. 5, 1993, pp. 569-621.

"Iontophoresis: Electrorepulsion and Electroosmosis," Guy et al., Journal of Controlled Release 64 (2000) 129-132.

"Treatment of Common Cutaneous Herpes Simplex Virus Infections," Emmert, American Family Physician, vol. 61, No. 6, Mar. 15, 2000, pp. 1697-1704.

"Gelatin-stabilised Microemulsion-Based Organogels: Rheology and Application in Iontophoretic Transdermal Drug Delivery," Kantaria et al., Journal of Controlled Release 60 (1999) 355-365.

"Electrorepulsion Versus Electroosmosis: Effect of pH on the Iontophoretic Flux of 5-Fluorouracil," Merino et al., Pharmaceutical Research, vol. 16, No. 6 (1999).

"Azelaic Acid: Potential as a General Antitumoural Agent," Breathnach, Medical Hypotheses (1999) 52(3) 221-226.

"Treatment of Mucocutaneous Herpes Simplex Virus Infections Unresponsive to Acyclovir with Topical Foscarnet Cream in AIDS Patients: A Phase I/II Study," Javaly et al., Journal of Acquired Immune Deficiency Syndromes 21:301-306.

"Efficacy and Safety of Azelaic Acid and Glycolic Acid Combination Therapy Compared with Tretinoin Therapy for Acne," Spellman et al., Clinical Therapeutics, vol. 20, No. 4, 1998, pp. 711-721.

"Passive Versus Electrotransport-Facilitated Transdermal Absorption of Ketorolac," Park et al., Clinical Pharmacology & Therapeutics, vol. 63, No. 3, pp. 303-315.

"Soriudine Versus Acyclovir for Treatment of Dermatomal Herpes Zoster in Human Immunodeficiency Virus-Infected Patients: Results from a Randomized, Controlled Clinical Trial," Gnann et al., Antimicrobial Agents and Chemotherapy, vol. 42, No. 5, May 1998, pp. 1139-145.

"Azelaic Acid 20% Cream (AZELEX®) and the Medical Management of Acne Vulgaris," Gibson, Dermatology Nursing, vol. 9, No. 5, pp. 339-344.

"Sorivudine: A Promising Drug for the Treatment of Varicella-Zoster Virus Infection," Whitley, Neurology 1995; 45 (Supp. 8), pp. S73-S75.

"Antiherpesviral and Anticellular Effects of 1-β-D-Arabinofuranosyl-E-5-(2-Halogenovinyl) Uracils," Machida et al., Antimicrobial Agents and Chemotheraphy, Jul. 1981, pp. 47-52.

"Herpes Simplex," American Academy of Dermatology, 1987, Revised 1991, 1993.

"'Common Cold' Virus is Near," Haney, The Associated Press, Jan. 15, 2000.

"New Medicines Move to Eradicate Acne," Hemphill, The New York Times, Feb. 29, 2000.

"Warts," American Academy of Dermatology, American Academy of Dermatology, 1997, Revised 1991, 1993.

"Psoriasis," American Academy of Dermatology, 1994.

"Eczema/Atopic Dermatitis," American Academy of Dermatology, 1987, Revised 1991, 1993, 1995.

"Skin Cancer: An Undeclared Epidemic," American Academy of Dermatology, 1988, Revised 1989, 1993, 1994.

Waggoner et al, Biophysical Journal, vol. 33, 292a (1981).

CYANINE DYES AS LABELING REAGENTS FOR DETECTION OF BIOLOGICAL AND OTHER MATERIALS BY LUMINESCENCE METHODS

This application is a division of application Ser. No. 09/740,486, filed Dec. 19, 2000, pending, which is a continuation of Ser. No. 08/745,712 filed Nov. 12, 1996 now U.S. Pat. No. 6,225,050 which is a continuation-in-part of Ser. No. 07/831,759 filed Sep. 22, 1992 now U.S. Pat. No. 5,627,027 which is a continuation of Ser. No. 06/854,347 filed Apr. 18, 1986 abandoned, the entire contents of which are hereby incorporated by reference in this application.

This invention was made in part under National Institutes of Health contract number 5R01NS19353-02. The United States government may have rights in this invention.

BACKGROUND OF THE INVENTION

Cyanine and related polymethine dyes having light absorbing properties have been employed in photographic films. Although such dyes require light absorbing properties, they do not require luminescence (fluorescent or phosphorescent) properties. Cyanine dyes having luminescence properties heretofore have had very limited utilization. One such utilization involved specifically labeling the sulfhydryl group of proteins. In one report, Salama, G., Waggoner, A. S., and Abramson, J. have reported under the title Sulfhydryl Reagent Dyes Trigger the Rapid Release of $Ca^{2+}$ from Sarcoplasmic Reticulum Vesicles (SR), *Biophysical Journal,* 47, 456a (1985) that cyanine chromophores having an iodoacetyl group was used to form covalent bonds with sulfhydryl groups on the Sarcoplasmic Reticulum protein at Ph 6.7 to trigger $Ca^{2+}$ release. The report also stated that fluorescent dyes were used to label and isolate those proteins.

In a report of A. S. Waggoner, P. L. Jenkins and J. P. Carpenter entitled The Kinetics of Conformational Changes in a Region of the Rhodopsin Molecule Away From the Retinylidene Binding Site, *Biophysical Journal,* 33, 292a (1981), the authors state that the sulfhydryl group on the F1 region of cattle rhodopsin has been covalently labeled with a cyanine dye having absorbance at 660 nm. Again, this report used cyanine dyes for labeling specifically the sulfhydryl group of a protein, but does not disclose that fluorescent dyes were used.

An article entitled International workshop on the application of fluorescence photobleaching techniques to problems in cell biology, Jacobson K., Elson E., Koppel D., Webb W. Fed. Proc. 42:72–79 (1983), reports on a paper delivered by A. Waggoner relating to cyanine-type fluorescent probes which can be conjugated to proteins and can be excited in the deeper red region of the spectrum.

The only cyanine probes mentioned in any of the above three reports are those which covalently attach specifically to the sulfhydryl group of a protein. The only specific cyanine compound mentioned is one having an iodoacetyl group, which group causes the cyanine dye to be covalently reactive with a sulfhydryl group. None of the articles listed above discloses the covalent reaction of a cyanine dye with any material other than a protein or with any group on a protein other than a sulfhydryl group.

However, many non-protein materials do not have sulfhydryl groups and many proteins do not have a sufficient number of sulfhydryl groups to make these groups useful for purposes of fluorescence probing. Furthermore, sulfhydryl groups (—SHSH—) are easily oxidized to disulfides (—S—S—) in the presence of air and thereby become unavailable for covalent attachment to a fluorescence probe.

SUMMARY OF THE INVENTION

In accordance with the present invention, cyanine and related polymethine dyes have been developed having substituent groups which are covalently reactive under suitable reaction conditions with amine (—$NH_2$) and hydroxy (—OH) groups on proteins, nucleic acids, cells, sugars, carbohydrates and other materials for purposes of fluorescence and phosphorescence detection of those materials. The present invention offers considerable advantages over the use of the iodoacetyl cyanine dye of the prior art and its specific reactivity with sulfhydryl groups. Amine and hydroxy groups are more prevalent in proteins and other materials than are sulfhydryl groups and are more stable. Thereby, when fluorescent cyanine dyes are used for detecting the presence of certain proteins, a stronger fluorescent or phosphorescent light intensity signal will be given off because a larger number of dye molecules can be attached to the protein which is being probed. Furthermore, amine and hydroxy groups are more easily added to components which it is desired to label, such as polymer particles, which do not naturally contain either sulfhydryl, amine or hydroxy groups.

According to the present invention, the iodoacetyl cyanine dye which was used in the prior art at a pH of 6.7 to react with sulfhydryl groups can be sometimes used in a process under appropriate temperature and reaction time conditions at pH's above 7 at which they will covalently react with neutral amine and hydroxy groups.

This invention also relates to a method wherein luminescent cyanine dyes which contain a group which is covalently reactive with amine or hydroxy groups are used to label proteins, nucleic acids, cells, sugars, carbohydrates or other materials having an amine or hydroxy group in a mixture so that the presence and amount of labeled protein or other material can be detected after the labeled components have been separated by chromatographic methods. According to the above cited references, apparently the sulfhydryl group was selected for covalent reaction specifically because there are so few of these groups on a protein molecule and because in some cases the sulfhydryl group plays a significant role in the function of the protein. Therefore, it was possible for the authors to attempt to ascertain the specific location of a sulfhydryl group on a protein structure. Also, in those references the sulfhydryl-specific dye was used as a probe to detect or to produce structural changes in a specific protein. Then, in order to interpret a change in light absorption by the dye or the calcium ion released by dye binding, it was necessary to know where the probe is bound.

Because there are so few sulfhydryl groups on most protein molecules, those groups may not be sufficiently numerous to provide adequate total luminescence for detection studies. In contrast, amine and hydroxy groups are significantly more numerous and are widely dispersed on a protein molecule enabling a fluorescent probe to be attached to multiple sites on the molecule, thereby precluding interpretation of light absorption or fluorescence changes, by facilitating the detection of the protein. Therefore, the method of the present invention is clearly in contrast to the method of the references cited above.

The present invention relates to the labeling with luminescent polymethine cyanine and related polymethine dyes, such as merocyanine, styryl and oxonol, of proteins, sugars, carbohydrates and other materials, including nucleic acids, DNA, drugs, toxins, blood cells, microbial materials, particles, etc., at an amine or hydroxy site on those materials. The dyes are advantageously soluble in aqueous or other medium in which the labeled material is contained. The present invention relates to a two-step labeling process in addition to a single step labeling process. In the two-step labeling process, a primary component, such as an antibody, can be labeled at sites thereon, including amine, hydroxy or sulfhydryl sites, and the labeled component is used as the probe for a secondary component, such as an antigen for which the antibody is specific.

In the prior art discussed above, specificity of site of attachment by a cyanine probe was achieved by using a probe which is covalently reactive with a sulfhydryl group. According to the two-step method of the present invention, cyanine and related probes can be reacted in a first step with amine, sulfhydryl or hydroxy groups on a first component, such as an antibody, and then the antibody can achieve the desired specificity in a second component, such as an antigen, in a second or staining step, the specificity being determined by the antigen site of attachment to the antibody.

The present invention is directed also to the luminescent polymethine cyanine and related compounds which contain groups enabling them to be covalently attached to amine or hydroxy groups on a target molecule. It is directed to monoclonal antibodies and other components labeled with these luminescent cyanine compounds which are capable of being probes for antigens. When the target is a type of cell, the present invention can be employed to measure the amount of labeled antibodies which are attached to that type of cell. The measurement can be made by determining the relative brightness or dimness of the luminescence of the cells.

The present invention can be employed to determine the concentration of a particular protein or other component in a system. If the number of reactive groups on a protein which can react with a probe is known, the fluorescence per molecule can be known and the concentration of these molecules in the system can be determined by the total luminescence intensity of the system.

The method can be employed to quantify a variety of proteins or other materials in a system by labeling all of a mixture of proteins in the system and then separating the labeled proteins by any means, such as chromatographic means. The amount of separated proteins that are luminescent can then be determined. In chromatographic detection systems, the location of the dye on the labeled material can be ascertained.

This invention can also be employed to determine the number of different cells which are tagged by an antibody. This determination can be made by tagging a plurality of types of cells in a system, and then separating the tagged cells outside of the system. Also, tagged cells can be separated from non-tagged cells outside of the system.

Another embodiment of the present invention comprises a multiparameter method employing a plurality of luminescent cyanine or related dyes attached respectively to a plurality of different primary components, such as antibodies, each specific for a different secondary component, such as an antigen, in order to identify each of a plurality of said antigens in a mixture of antigens. According to this embodiment, each of said antibodies is separately labeled with a dye having different light absorption and luminescence wavelength characteristics than the dye used for labeling the other probes. Then, the labeled antibodies are all added to a biological preparation being analyzed containing secondary components, such as antigens, which can be respectively stained by particular labeled antibodies. Any unreacted dye materials may be removed from the preparation as by washing, if they interfere with the analysis. The biological preparation is then subjected to a variety of excitation wavelengths, each excitation wavelength used being the excitation wavelength of a particular conjugated dye. A luminescence microscope or other luminescence detection system, such as a flow cytometer or fluorescence spectrophotometer, having filters or monochrometers to select the rays of the excitation wavelength and to select the wavelengths of luminescence is employed to determine the intensity of rays of the emission wavelength corresponding to the excitation wavelength. The intensity of luminescence at wavelengths corresponding to the emission wavelength of a particular conjugated dye indicates the quantity of antigen which has been bound the antibody to which the dye is attached. If desired, a light absorption detection method can be employed. The two-step method of the invention can be applied to any system in which a primary material conjugated with a dye is used in a luminescence or light absorption detection system to detect the presence of another material to which the primary material-dye conjugate is directed. For example, the dye can be conjugated to a fragment of DNA or RNA to form a dye conjugated DNA or RNA fragment which is then directed to a main strand of DNA or RNA to which the piece is complementary. The same test method can be employed to detect the presence of any complementary main strand of DNA.

The cyanine and related dyes of this invention are especially well adapted for the analysis of a mixture of components wherein dyes of a variety-of excitation and emission wavelengths are required because specific cyanine and related dyes can be synthesized having a wide range of excitation and emission wavelengths. Specific cyanine and related dyes having specific excitation and emission wavelengths can be synthesized by varying the number of methine groups or by modifying the cyanine ring structures. In this manner, it is possible to synthesize dyes having particular excitation wavelengths to correspond to a particular excitation light source, such as a laser, e.g., a HeNe laser or a diode laser.

This invention relates to the covalent reaction of highly luminescent and highly light absorbing cyanine and related dye molecules under reaction conditions to amine and hydroxy groups on proteins, peptides, sugars, carbohydrates, nucleic acids, derivatized nucleic acids, lipids, certain other biological molecules, biological cells, as well as to non-biological materials, such as soluble polymers, polymeric particles, and other particles and surfaces. Because luminescence involves highly sensitive optical techniques, the presence of these dye "labels" can be detected and quantified even when the label is present in very low amounts. Thus the dye labeling reagents can be used to measure the quantity of a material that has been labeled. The most useful dyes are highly light absorbing ($\epsilon$=100,000 to 250,000 liters per mole centimeter, or higher) and very luminescent and they have quantum yields of at least 0.1 to 0.8, or more. The qualities apply to the dyes themselves and to the dyes conjugated to a labeled material.

An important application for these color labeling reagents is the production of luminescent monoclonal antibodies. Monoclonal antibodies are protein molecules that bind very tightly and very specifically to certain chemical sites or "markers" on cell surfaces or within cells. These antibodies, therefore, have an enormous research and clinical use for identifying certain cell types (e.g., HLA classification, T-cell subsets, bacterial and viral classification, etc.) and diseased cells. In the past, the amount of antibody bound to a cell has been quantified by tagging the antibody in various ways. Tagging has been accomplished with a radioactive label (radio immune assay), an enzyme (ELISA techniques), or a fluorescent dye (usually fluorescein, rhodamine, Texas Red or phycoerythrin). Most manufacturers and users of clinical antibody reagents would like to get away from the problems involved in the use of radioactive tracers so luminescence is considered one of the most promising alternatives. In fact, many companies now market fluorescein, Texas Red, rhodamine and phycoerythrin labeled monoclonal antibodies.

In recent years, optical/electronic instrumentation for detecting fluorescent antibodies on cells has become more sophisticated. For example, flow cytometry can be used to measure the amount of fluorescent antibody on individual cells at a rate up to 5,000 cells per second. Microscopy and solution fluorescence techniques have also advanced. These instruments can excite fluorescence at many wavelengths of the UV, visible, and near IR regions of the spectrum. Yet most of the useful fluorescent labeling reagents available today can be excited only in the 400–580 nm region of the spectrum. The exceptions are some of the phycobiliprotein-type pigments isolated from marine organisms which can be covalently attached to proteins and which can be excited at somewhat longer wavelengths. Therefore, there is a large spectral window ranging from 580 to roughly 900 nm where new labeling reagents' need to become available for labeling biological and non-biological materials for analysis with now available instrumentation. New reagents excitable in this spectral region would make it possible to perform color luminescence analyses of markers on cells because antibodies with different specificities could each be tagged with a different colored fluorescent dye. Thus the presence of several markers could be determined simultaneously for each cell analyzed.

This invention also relates to the luminescent (fluorescent or phosphorescent) cyanine, merocyanine, styryl and oxonol dyes themselves that can be covalently linked to biological and non-biological materials. Merocyanine, styryl and oxonol dyes are considered to be related to cyanine dyes for purposes of this invention. The present invention also relates to conjugate complexes comprised of components selected from the group consisting of nucleic acid molecules (DNA and RNA), proteins, cells, sugars and carbohydrates that are labelled with the luminescent cyanine dyes described herein. The new labeling reagents themselves, but more particularly when conjugated to a labeled component, can be excited by light of first defined wavelengths, e.g. by light in wavelength regions of the spectrum ranging from 450 nm to 900 nm. Background fluorescence of cells generally occurs at a lower wavelength. Therefore, the labeling reagents will distinguish over background fluorescence. Particularly of interest are the derivatives that absorb light at 633 nm since they can be excited by inexpensive, intense, stable, long-life, HeNe laser sources. Light of second defined wavelengths that is fluoresced or phosphoresced by the labeled component can then be detected. The fluoresced or phosphoresced light generally has a greater wavelength than the excitation light. The detection step can employ a luminescence microscope having a filter for absorption of scattered light of the excitation wavelength and for passing the wavelength that corresponds to the luminescence corresponding to the particular dye label used with the specimen. Such an optical microscope is described in Ser. No. 711,065, filed Mar. 12, 1985.

Not all cyanine and related dyes are luminescent. However, the dyes of this invention include those of the cyanine and related dyes which are luminescent. They are relatively photostable and many are soluble in the reaction solution, preferably a water solution. The conjugated dyes themselves, but more particularly when conjugated to a labeled component, have molar extinction coefficients ($\epsilon$) of at least 50,000, and preferably at least 120,000 liters per mole centimeter. The extinction coefficient is a measure of the capability of the molecules to absorb light. The conjugated dyes of this invention have quantum yields of at least 5 percent and preferably at least 20 percent. In addition, the conjugated dyes of this invention absorb and emit light in the 400 to 900 nm spectral range, and preferably in the 600 to 900 nm spectral range.

BRIEF DESCRIPTION OF THE FIGURES

The present invention can be better understood by reference to the figures in which.

BACKGROUND PROCEDURES

Figures 1A, 1B:
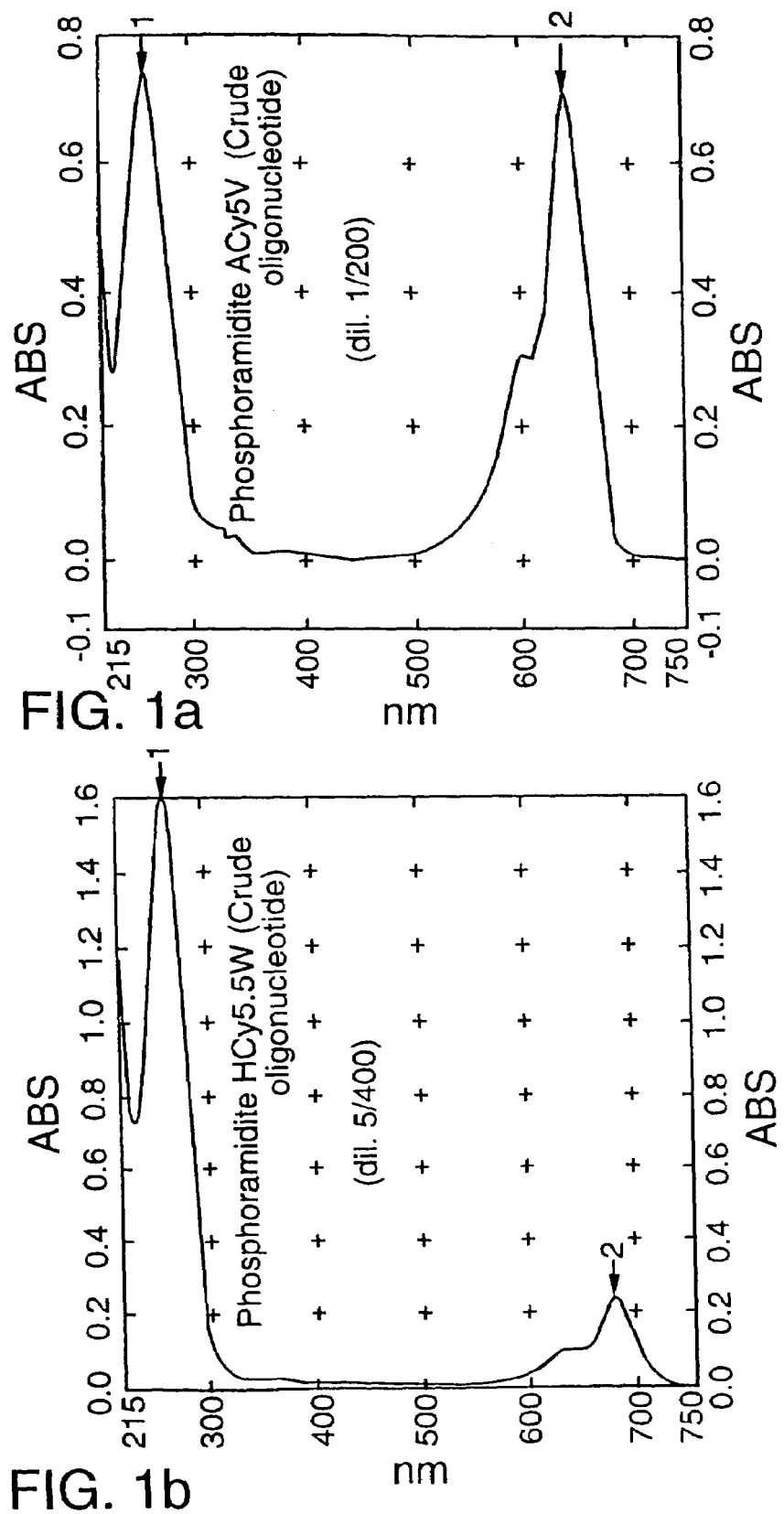
FIGS. 1(a) and (b) are absorbance scans of oligonucleotide synthesis products after deprotection and ethanol precipitation of the DNA but before HPLC purification.

Luminescent probes are valuable reagents for the analysis and separation of molecules and cells and for the detection and quantification of other material. A very small number of luminescent molecules can be detected under optimal circumstances. Barak and Webb visualized fewer than 50 fluorescent lipid analogs associated with the LDL reception of cells using a SIT camera, J. Cell Biol. 90:595–604 (1981). Flow cytometry can be used to detect fewer than 10,000 fluorescein molecules associated with particles or certain cells (Muirhead, Horan and Poste, Bio/Technology 3:337–356 (1985)). Some specific examples of the application of fluorescent probes are (1) identification and separation of subpopulations of cells in a mixture of cells by the techniques of fluorescence flow cytometry, fluorescence-activated cell sorting and fluorescence microscopy; (2) determination of the concentration of a substance that binds to a second species (e.g., antigen-antibody reactions) in the technique of fluorescence immunoassay; (3) localization of substances in gels and other insoluble supports by the techniques of fluorescence staining. These techniques are described by Herzenberg et al., "Cellular Immunology," 3rd ed., chapt. 22; Blackwell Scientific Publications, 1978 (fluorescence-activated cell sorting); and by Goldman, "Fluorescence Antibody Methods," Academic Press, New York, (1968) (fluorescence microscopy and fluorescence staining); and in Applications of Fluorescence in the Biomedical Sciences, ed. Taylor et al., Alan Liss Inc., (1986).

When employing fluorescers for the above purposes, there are many constraints on the choice of the fluorescer. One constraint is the absorption and emission characteristics of the fluorescer, since many ligands, receptors, and materials in the sample under test, e.g. blood, urine, cerebrospinal fluid, will fluoresce and interfere with an accurate determination of the fluorescence of the fluorescent label. This phenomenon is called autofluorescence or background fluorescence. Another consideration is the ability to conjugate the fluorescer to ligands and receptors and other biological and non-biological materials and the effect of such conjugation on the fluorescer. In many situations, conjugation to another molecule may result in a substantial change in the fluorescent characteristics of the fluorescer and, in some cases, substantially destroy or reduce the quantum efficiency of the fluorescer. It is also possible that conjugation with the fluorescer will inactivate the function of the molecule that is labeled. A third consideration is the quantum efficiency of the fluorescer which should be high for sensitive detection. A fourth consideration is the light absorbing capability, or extinction coefficient, of the fluorescers, which should also be as large as possible. Also of concern is whether the fluorescent molecules will interact with each other when in close proximity, resulting in self-quenching. An additional concern is whether there is non-specific binding of the fluorescer to other compounds or container walls, either by themselves or in conjunction with the compound to which the fluorescer is conjugated.

The applicability and value of the methods indicated above are closely tied to the availability of suitable fluorescent compounds. In particular, there is a need for fluorescent substances that emit in the longer wavelength visible region (yellow to near infrared), since excitation of these chromophores produces less autofluorescence and also multiple chromophores fluorescing at different wavelengths can be analyzed simultaneously if the full visible and near infrared regions of the spectrum can be utilized. Fluorescein, a widely used fluorescent compound, is a useful emitter in the green region although in certain immunoassays and cell analysis systems background autofluorescence generated by excitation at fluorescein absorption wavelengths limits the detection sensitivity. However, the conventional red fluorescent label rhodamine has proved to be less effective than fluorescein. Texas Red is a useful labeling reagent that can be excited at 578 nm and fluoresces maximally at 610 nm.

Phycobiliproteins have made an important contribution because of their high extinction coefficient and high quantum yield. These chromophore-containing proteins can be covalently linked to many proteins and are used in fluorescence antibody assays in microscopy and flow cytometry. The phycobiliproteins have the disadvantages that (1) the protein labeling procedure is relatively complex; (2) the protein labeling efficiency is not usually high (typically an average of 0.5 phycobiliprotein molecules per protein); (3) the phycobiliprotein is a natural product and its preparation and purification is complex; (4) the phycobiliproteins are expensive; (5) there are at present no phycobiliproteins available as labeling reagents that fluoresce further to the red region of the spectrum than allophycocyanine, which fluoresces maximally at 680 nm; (6) the phycobiliproteins are large proteins with molecular weights ranging from 33,000 to 240,000 and are larger than many materials that it is desirable to label, such as metabolites, drugs, hormones, derivatized nucleotides, and many proteins including antibodies. The latter disadvantage is of particular importance because antibodies, avidin, DNA-hybridization probes, hormones, and small molecules labeled with the large phycobiliproteins may not be able to bind to their targets because of steric limitations imposed by the size of the conjugated complex.

Other techniques involving histology, cytology, immunoassays would also enjoy substantial benefits from the use of a fluorescer with a high quantum efficiency, absorption and emission characteristics at longer wavelengths, having simple means for conjugation and being substantially free of nonspecific interference.

Outline of Invention

This invention employs reactive fluorescent cyanine and related dyes having relatively large extinction coefficients and high quantum yields for the purpose of detection and quantification of labeled components. Fluorescent cyanine and related dyes can preferably be used to label biological materials such as nucleic acids, proteins, carbohydrates, sugars, cells and combinations thereof. More specifically, the cyanine type dyes of the invention can label antibodies, antigens, avidin, peptides, derivatized nucleotides, bacteria, viruses, blood cells, tissue cells, hormones, lymphokines, trace biological molecules, toxins and drugs. Fluorescent dyes can also be used to label non-biological materials, such as soluble polymers and polymeric particles, glass, monomers, drugs and other surfaces and particles which contain or are derivatized to contain functionalities capable of binding covalently to the amino, hydroxy or sulfhydryl reactive nucleophiles of the cyanine dye molecule. The component being labeled can be in a mixture including other materials. The mixture, in which the labeling reaction occurs, can be a liquid mixture, particularly a water mixture. The detection step can occur with the mixture in a liquid or dry condition, such as a microscope slide.

This invention requires cyanine dyes to be modified by the incorporation into the cyanine molecule of a reactive group that will covalently attach to a target molecule, preferably at an amine or hydroxy site, and in some instances at a sulfhydryl site. This invention also employs modification or use of cyanine and related dye structures to enhance their solubility in the test liquid to help prevent aggregation of the dye on the surface of proteins that are being labeled and to help prevent nonspecific binding of labeled materials to biological materials and to surfaces and assay apparatus.

The cyanine and related dyes offer an important advantage over existing fluorescent labeling reagents. First, cyanine and related dyes have been synthesized that absorb and emit in a region of the spectrum ranging from 400 to nearly 1100 nm. Thus reactive derivatives of these dyes can be made for assays that require simultaneous measurement of a number of labeled materials. Multicolor (or multiparameter) analysis of this sort may be desirable for the sake of simplicity, cost effectiveness, or for determining ratios of different labeled species on each particle in a complex mixture of particles (e.g., ratios of antigen markers on individual blood cells in a complex mixture by multiparameter flow cytometry or fluorescence microscopy). Second, many cyanine and related dyes strongly absorb and fluoresce light. Third, many cyanine and related dyes are relatively photostable and do not rapidly bleach under the fluorescence microscope. Fourth, cyanine and related dye derivatives can be made which are simple and effective coupling reagents. Fifth, many structures and synthetic procedures are available and the class of dyes is versatile. Therefore, many structural modifications can be made to make the reagents more or less water soluble. Their charge can be changed so they will not perturb the molecule to which they are attached and so nonspecific binding can be reduced. Sixth, unlike the phycobiliproteins the cyanine type dyes are relatively small (molecular weight=1,000) so they don't sterically interfere appreciably with the ability of the labeled molecule to reach its binding sight or carry out its function.

Thus cyanine type dye labeling agents offer many potential advantages. These dyes can be used to selectively label one or more components in a liquid, especially an aqueous liquid. The labeled component can then be detected by optical or luminescence methods. Alternately, the labeled component can then be used to stain a second component for which it has a strong affinity, and the presence of the second component is then detected by optical or luminescence methods. In this case, the dye is reacted with an amine, hydroxy or sulfhydryl group on the labeled component. For example, the labeled component can be an antibody and the stained component for which it has a strong affinity can be a biological cell, an antigen or a hapten, or a biological cell or particle containing said antigen or hapten. In another example, the labeled component is avidin and the stained component can be biotinylated materials. Also, lectins conjugated with polymethine cyanine type dyes can be used to detect and quantify specific carbohydrate groups. In addition, luminescent cyanine and related dyes can be attached to fragments of DNA or RNA. The labeled fragments of DNA or RNA can be used as fluorescent hybridization probes to identify the presence and quantity of specific complementary nucleotide sequences in samples of DNA or RNA. Also, the dye can be attached to a hormone or ligand (such as a hormone, protein, peptide, lymphokine, metabolite) which in turn can be attached to a receptor.

Reactive Cyanine Dyes are Described in Patents for Other Uses

Miraha et al. (U.S. Pat. No. 4,337,063), and Masuda et al. (U.S. Pat. No. 4,404,289 and U.S. Pat. No. 4,405,711) have synthesized a variety of cyanine dyes possessing N-hydroxysuccinimide active ester groups. These patents show that these reagents can be used as photographic sensitizers. The possible fluorescence properties of these reagents are not mentioned in the patents and, indeed, fluorescence is not required for their process. Most of the dyes mentioned in those patents are only weakly fluorescent, they are not especially photostable, and their solubility properties are not optimal for many uses that would involve fluorescence detection of labeled materials.

Exekiel et al. (British Patent 1,529,202) have presented numerous cyanine dye derivatives that can be used as covalently reacting molecules. The reactive group used in these reagents are azine groups to which the mono- and dichloro-triazine groups belong. The British patent relates to the development and use of these reagents as photographic film sensitizers. Fluorescence is not required for the process and most of the reagents described are not fluorescent. The British patent does not relate to the development and use of reactive cyanine dyes for the purpose of detecting and quantifying labeled materials.

Description of the Preferred Embodiments

The present invention pertains to methods for covalently attaching luminescent cyanine and cyanine-type dyes to biological materials, non-biological molecules and macromolecules, and particles in order to make the material that has been labeled luminescent so that the labeled material can be detected and/or quantified by luminescence detection methods.

This invention relates to a method for the detection of a component in a liquid comprising adding to said liquid a dye selected from the group consisting of cyanine, merocyanine, oxonol and styryl dyes which is soluble in the liquid and contains a substituent to make it covalently reactive with amine and hydroxy groups, and possibly to sulfhydryl groups, on said component so that it labels said component. The labeled component is then detected and/or quantified by luminescence or light absorption methods. If the labeled component is an antibody, DNA fragment, hormone, lymphokine, or drug, the labeled component can be used to identify the presence of a second component to which it binds, and then the second component can be detected and/or quantified.

Any available luminescence or light absorbing detecting step can be employed. For example, the detecting step can be an optical detecting step wherein the liquid is illuminated with light of first defined wavelengths. Light at second defined wavelengths that is fluoresced or phosphoresced by the labeled component is then detected. The detection also can be by optical light absorption. For example, the detecting step can comprise passing light of first defined wavelengths through the liquid and then ascertaining the wavelength of the light that is transmitted by the liquid.

If desired, the detecting step can comprise chemical analysis to chemically detect attachment of the cyanine or related chromophore to the component.

The basic structures of cyanine, merocyanine, styryl and oxonol dyes that can be modified to create covalent labeling reagents are shown below wherein the dotted lines each represent the carbon atoms necessary for the formulation of the dye.

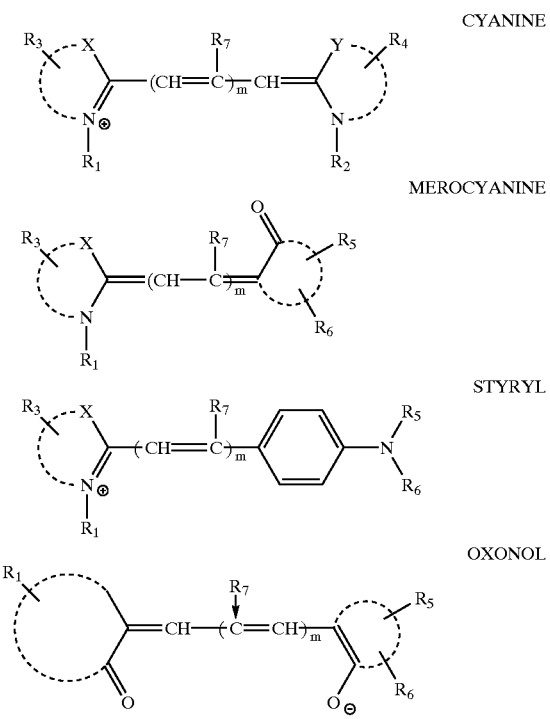

The following are more specific examples of polymethine cyanine type dyes:

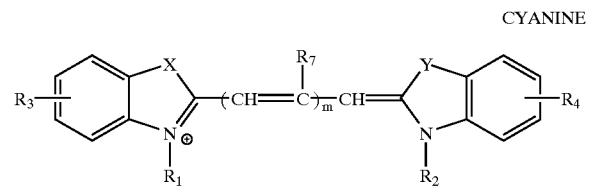

CYANINE

-continued

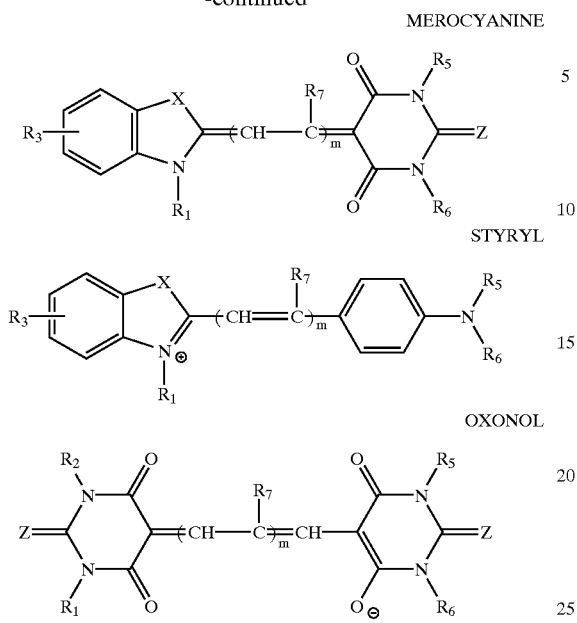

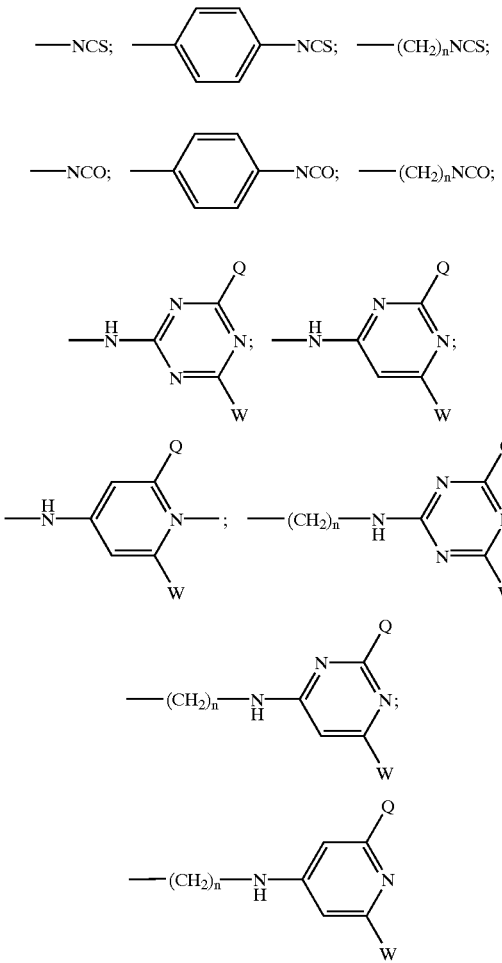

In these structures

X and Y are selected from the group consisting of O, S and $CH_3$—C—$CH_3$;

Z is selected from the group consisting of O and S;

m is an integer selected from the group consisting of 1, 2, 3 and 4 and, preferably an integer from 1–3.

In the above formulas, the number of methine groups determines in part the excitation color. The cyclic azine structures can also determine in part the excitation color. Often, higher values of m contribute to increased luminescence and absorbance. At values of m above 4, the compound becomes unstable. Thereupon, further luminescence can be imparted by modifications at the ring structures. When m=2, the excitation wavelength is about 650 nm and the compound is very fluorescent. Maximum emission wavelengths are generally 15–100 nm greater than maximum excitation wavelengths.

At least one, preferably only one, and possibly two or more of said $R_1$, $R_2$, $R_3$, $R_4$, $R_5$, $R_6$ and $R_7$ groups in each molecule is or contains a reactive group covalently reactive with amine, protected or unprotected hydroxy or sulfhydryl nucleophiles for attaching the dye to the labeled component. For certain reagents, at least one of said $R_1$, $R_2$, $R_3$, $R_4$, $R_5$, $R_6$ and $R_7$ groups on each molecule may also be a group that increases the solubility of the chromophore, or affects the selectivity of labeling of the labeled component or affects the position of labeling of the labeled component by the dye.

Reactive groups that may be attached directly or indirectly to the chromophore to form $R_1$, $R_2$, $R_3$, $R_4$, $R_5$, $R_6$ and $R_7$ groups may include reactive moieties such as groups containing isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, acid halide, hydroxysuccinimide ester, hydroxysulfosuccinimide ester, imido ester, hydrazine, axidonitrophenyl, azide, 3-(2-pyridyl dithio)-proprionamide, glyoxal and aldehyde.

Specific examples of $R_1$, $R_2$, $R_3$, $R_4$, $R_5$, $R_6$ and $R_7$ groups that are especially useful for labeling components with available amino-, hydroxy-, and sulfhydryl groups include:

where at least one of Q or W is a leaving group such as I, Br or Cl,

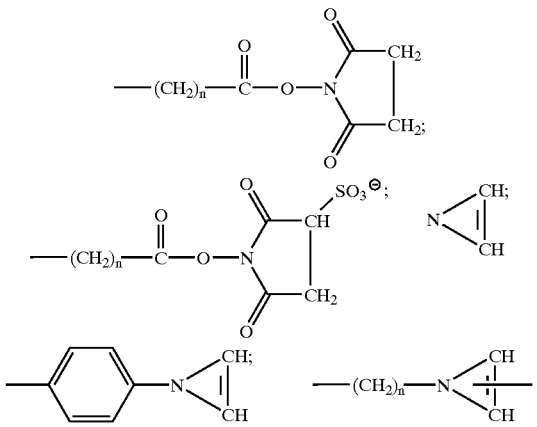

Specific examples of $R_1$, $R_2$, $R_3$, $R_4$, $R_5$, $R_6$ and $R_7$ groups that are especially useful for labeling components with available sulfhydryls which can be used for labeling antibodies in a two-step process:

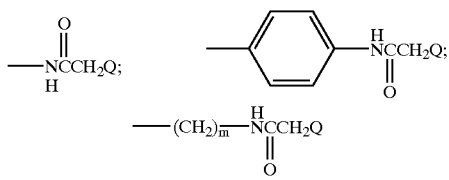

where Q is a leaving group such as I or Br,

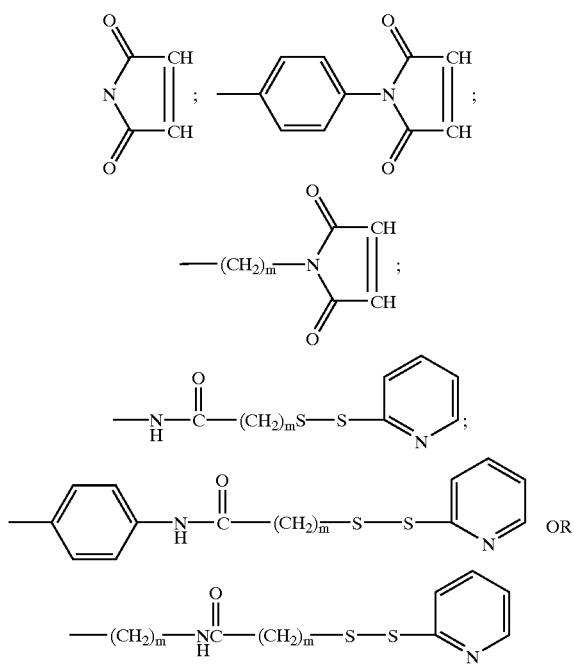

where n is 0 or an integer.

Specific examples of $R_1$, $R_2$, $R_3$, $R_4$, $R_5$, $R_6$ and $R_7$ groups that are especially useful for labeling components by light-activated cross linking include:

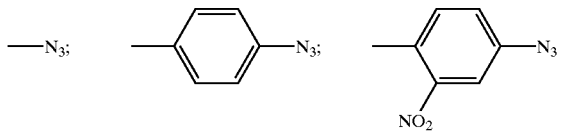

For the purpose of increasing water solubility or reducing unwanted nonspecific binding of the labeled component to inappropriate components in the sample or to reduce the interactions between two or more reactive chromophores on the labeled component which might lead to quenching of fluorescence, the $R_1$, $R_2$, $R_3$, $R_4$, $R_5$, $R_6$ and $R_7$ groups can be selected from the well known polar and electrically charged chemical groups. When any of the $R_3$, $R_4$ or $R_7$ groups are not a reactive group they may be hydrogen, $C_1$–$C_4$ alkyl, or the group -E-F, a polar group, wherein F is hydroxy, protected hydroxy, sulfonate, sulfate, carboxylate, lower alkyl substituted amino or quaternary amino and wherein E is a spacer group such as —$(CH_2)_n$— where n is 0, 1, 2, 3, 4 or 5. If $R_1$, or $R_4$ is not a reactive group it can be the E-F group, wherein n of the spacer is 1, 2, 3, 4 or 5, or $C_1$–$C_4$ alkyl. Useful examples include alkyl sulfonate; —$(CH_2)_3$—$SO_3^-$; and —$(CH_2)_4$—$SO_3^-$.

The polymethine chain of the luminescent dyes of this invention may also contain one or more cyclic chemical groups that form bridges between two or more of the carbon atoms of the polymethine chain. These bridges might serve to increase the chemical or photostability of the dye and might be used to alter the absorption and emission wavelength of the dye or change its extinction coefficient or quantum yield. Improved solubility properties may be obtained by this modification.

In accordance with this invention the labeled component can be antibodies, proteins, peptides, enzyme substrates, hormones, lymphokines, metabolites, receptors, antigens, haptens, lectins, toxins, carbohydrates, sugars, oligosaccharides, polysaccharides, nucleic acids, deoxy nucleic acids, derivatized nucleic acids, derivatized deoxy nucleic acids, DNA fragments, RNA fragments, derivatized DNA fragments, derivatized RNA fragments, natural drugs, virus particles, bacterial particles, virus components, yeast components, blood cells, blood cell components, biological cells, noncellular blood components, bacteria, bacterial components, natural and synthetic lipid vesicles, synthetic drugs, poisons, environmental pollutants, polymers, polymer particles, glass particles, glass surfaces, plastic particles and plastic surfaces.

A cyanine or related chromophore can be prepared which when reacted with a component can absorb light at 633 nm and the detecting step can employ a helium neon laser that emits light at this wavelength of the spectrum. Also, a cyanine or related dye can be prepared which when reacted with a component can absorb light maximally between 700 nm and 900 nm and the detecting step can employ a laser diode that emits light in this region of the spectrum.

Selectivity

The reactive groups listed above are relatively specific for labeling particular functional groups on proteins and other biological or non-biological molecules, macromolecules, surfaces or particles provided that appropriate reaction conditions are used, including appropriate pH conditions.

Properties of the Reactive Cyanine and Merocyanine Dyes and their Products

The spectral properties of the dyes of this invention are not appreciably altered by the functionalization described in this specification. The spectral properties of labeled proteins and other compounds are also not very different from the basic dye molecule that has not been conjugated to a protein or other material. The dyes described in this invention alone or conjugated to a labeled material generally have large extinction coefficients ($\epsilon$=100,000 to 250,000), have quantum yields as high as 0.4 in certain cases, and absorb and emit light in the spectral range of 400 to 900 nm. Thus, they are especially valuable as labeling reagents for luminescence detection.

Optical Detection Methods

Any method can be employed for detecting a labeled or stained component. The detecting method can employ a light source that illuminates the mixture containing the labeled material with light of first defined wavelengths. Known devices are employed that detect light at second wavelengths that is transmitted by the mixture or is fluoresced or luminesced by the mixture. Such detection devices include fluorescence spectrometers, absorption spectrophotometers, fluorescence microscopes, transmission light microscopes and flow cytometers.

The method of this invention can also employ chemical analysis methods to detect attachment of the dye to the labeled component or components. Chemical analysis methods can include infrared spectrometry, NMR spectrometry, absorption spectrometry, fluorescence spectrometry, mass spectrometry and chromatographic methods.

EXAMPLES

Example 1

Reactive Dye I: Anhydro-1-methyl-1'-sulfobutyl-5-N-(3,5-dichloro-2,4,6-triazinyl)-aminomethyl-indodicarbocyanine Hydroxide

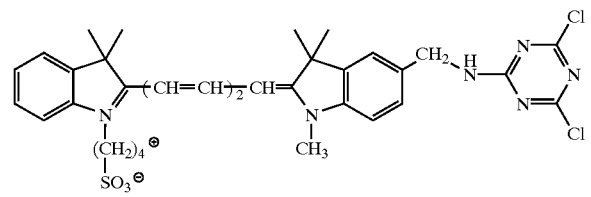

5-aminomethyl-1,3,3 trimethyl-2-methylene-indolenine (A) was synthesized according to Gale et al., Austr. J. Chem. 30:689–694 (1977). To a solution of 1.0 g cynuric chloride in dry methylene dichloride (40 ml) cooled to −12° C. under nitrogen was added dropwise with stirring a solution of 1.01 g of the aminomethyl-indolenine and 0.7 ml triethylamine in 60 ml methylene dichloride. The resulting brown solution was stirred for 1.5 hr. at 0° C., diluted with 100 ml methylene dichloride and washed with 80 ml water. The light red organic layer was washed with sat. salt solution, dried over sodium sulfate and concentrated to give 1.07 g of a reddish oil, (B).

2,3,3-trimethyl-(3H)-indole (0.48 g) and butane-1, 4-sultone (0.42 g) were heated for three hours in a stoppered flask at 120° C. The viscous semi-solid red mass was cooled, washed with ether (2×5 ml) and dried under vacuum. The product was dissolved in 10 ml acetic anhydride, and malonaldehyde dianil hydrochloride (0.77 g) was added. Heating at 125° C. for 30 minutes produced a solution of the anil intermediate which was cooled to room temperature. To this mixture was added a solution of (B) in 6 ml acetic anhydride, and it was again heated to 120° C. for 30 minutes. The resulting deep blue solution was cooled in ice and diluted with ether (40 ml). The precipitate was collected, washed with ether (10 ml), suspended in 8 ml ethanol and reprecipitated with ether (40 ml). The resulting semi-solid mass was chromatographed over 200 g of silica gel. Elution with chloroform-ethanol (4:1) gave 0.74 g of the pure dye I.

λ Abs=648 nm (Ethanol), $\epsilon_{648}$=198,000 (Ethanol), Max
λ Fluor=670 nm (Ethanol) Max

Example 2

Reactive Dye II: 1-(γ)-isothiocyanatopropyl-1'-methyl-indocarbocyanine Bromide,

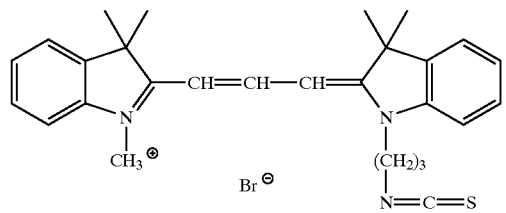

2,3,3-trimethyl-(3H)-indole and N-(3-bromo-propyl)-phthalimide (2.7 g) were heated at 110° C. in a sealed tube for four hours. The resulting red viscous mass solidified on cooling was washed with ether (2×20 ml) and then dried. The 1-(3-phthalimido propyl)-2,3,3-trimethyl indolinium bromide intermediate (C) was crystallized from ethanol-ether.

To produce the second intermediate (D), 2,3,3-trimethyl (3H)-indole (1.6 g) and methyl toluenesulfonate (1.9 g) were heated at 120° C. for 4 hours then cooled to room temperature. To form the cyanine dye intermediate, (E), N, N'-diphenyl formamidine (2 g) and acetic anhydride (25 ml) were added to the solution containing (D) and the mixture was heated with stirring for ten minutes at 110° C. then cooled. To this solution was added an ethanol solution containing intermediate (C). The mixture was heated to complete dissolution, triethylamine (1.5 ml) was added and the reaction mixture was again heated for 20 minutes at 125° C. An intense red solution resulted which was cooled, diluted with ether (30 ml) and filtered. The residue was washed thoroughly with ether, dried and then refluxed for four hours in 40% aqueous hydrobromic acid (50 ml). The product, (E), was precipitated by neutralization with sodium bicarbonate and collected by filtration, yielding 1.6 g of a semi-solid.

To an ice-cold solution of thiophosgene (0.45 ml) in 50 ml chloroform, was added drop-wise during thirty minutes a solution of the aminopropyl dye (E) (0.8 g) in chloroform (60 ml). The reaction mixture was stirred at 0–5° C. for one hour, allowed to warm to room temperature and stirred overnight. Solvent was removed by rotary evaporation, and the residue was chromatographed over silica gel (80 g). Elution with 5% ethanol in chloroform gave 0.15 g of pure final product. m.p. 109–112.

λ Abs=551 nm (Ethanol), $\epsilon_{551}$=107,000 (Ethanol), Max
λ Fluor=565 nm (Ethanol) Max

Example 3

Reactive Dye III: Anhydro-1-methyl-1'-(3-sulfopropyl)-5-iodoacetamido-indocarbocyanine Hydroxide

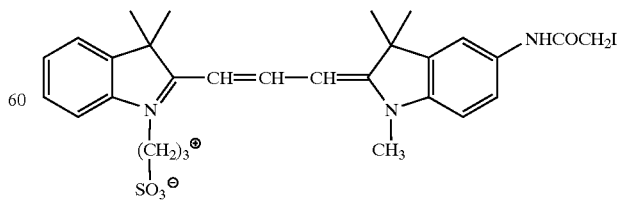

The first intermediate, 5-amino-1,3,3 trimethyl-2-methylene-indolenine (F) was prepared according to Gale and Wilshire (1974). The second intermediate, 5-chloroacetamido-1,3,3-trimethyl-2-methylene indolenine (G) was prepared by adding chloroacetylchloride (3.2 ml) in 180 ml dry benzene dropwise with stirring to 1.88 g of (F) in 180 ml dry benzene at 0–5° C. After stirring for 2 hr. more, 100 ml cold water was added. The aqueous layer was separated, made alkaline with ammonium hydroxide and extracted with ether. The ether extract was dried over anhydrous magnesium sulfate and concentrated. Recrystallization of the residue from dichloromethane-hexane (3–10) gave 2 g of yellow crystals, (G), m.p. 128–131° C.

The third intermediate, (H), was formed by the following procedure. A 1.7 g sample of 2,3,3-trimethyl-(3H)-indole and 1.3 g propane-1,3-sultone were heated in a sealed tube for 3 hr. at 100° C. The mixture solidified on cooling and was washed with ether (2×5 ml) and dried in vacuo. To this solid was added 2.0 g of N,N'-diphenyl formamidine and 12 ml acetic anhydride and the mixture was heated at 120° C. for 30 minutes. After cooling the solution was diluted with ether (30 ml), then filtered. The residue was crystallized from ethanol-ether to give 1.5 g of the anil, (H), m.p. 308–310° C.

A 1.3 g sample of anil (H) and 0.8 g of the chloroacetamido-indolenine, (G), were dissolved in 15 ml acetic anhydride, heated for 10 min. at 120° C. and cooled to room temperature. The solution was diluted with ether (40 ml). The red solid was collected and dried yielding 1.6 g of almost pure dye, (J). The chloroacetamido dye (J) (1.4 g) was refluxed for 2.5 hr. in methanol (150 ml) containing 1.4 g sodium iodide. After concentration of the reaction mixture to 10 ml, the product was precipitated by the addition of 200 ml acetone. The solid was collected, washed with acetone and ether to give 1.7 g of crude product. The dye was purified by chromatography over silica gel (80 g) eluting with 30% ethanol in chloroform which yielded 0.83 g of pure dye. m.p. 245–250.

λ Abs=565 nm (Ethanol), $\epsilon_{565}$=116,000 (Ethanol), Max
λ Fluor=590 nm (Ethanol) Max Example 4

Reactive Dye IV: Anhydro-1-(2-carboxy Ethyl)-1'-(4-sulfobutyl)-indotricarbocyanine Hydroxide N-hydroxysuccinimide Ester

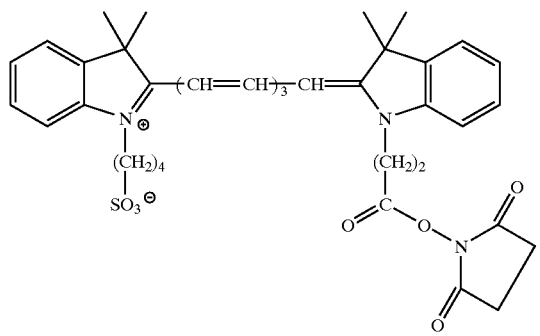

The intermediate (K), N-(2-carboxyethyl)-2,3,3-trimethyl-indolinium bromide, was prepared as follows. A sample of 5.8 g 2,3,3-trimethyl-(3H)-indole, 3-bromo-proprionic acid (5.1 g) and sodium iodide (5.0 g) were dissolved in 2-propanone (15 ml) and heated at reflux for 18 hours. The reaction mixture was cooled on ice, then diluted with 60 ml diethyl ether. After 2 hours on ice, the precipitate was collected and recrystallized from isopropanol. The product, (K), was a mauve-colored powder (4.5 g) with melting point of 166–167° C.

The cyanine dye intermediate (L), 1-(2-carboxyethyl)-1'-(4-sulfobutyl)-indotricarbocyanine, was prepared as follows. Anhydro-N-sulfobutyl-2,3,3-trimethyl-indolinium hydroxide (0.50 g) and glutaconaldehyde dianil hydrochloride (0.55 g) were dissolved in 10 ml of acetic anhydride, were refluxed for 20 minutes, cooled on ice and diluted with diethyl ether (40 ml). The resulting supernatant was decanted. The sticky residue was dissolved in acetic acid (5 ml) and reprecipitated with 25 ml ether. The supernatant was decanted. To the residue was added a solution of the above (K), N-carboxyethyl indolenene (0.5 g) in 15 ml methanol and then 0.25 ml triethylamine. This mixture was warmed on a hot plate for 45 minutes, cooled and diluted with 50 ml ether. The precipitate was collected, dissolved in a small volume of acetic acid and reprecipitated with ether. The crude product (0.8 g) was purified by chromatography over silica gel (3 cm×400 cm column) with methanol-chloroform (4:6) elution. The material collected (130 mg) was pure dye intermediate, (L), according to TLC.

The reactive N-hydroxysuccinimide ester of the indotricarbocyanine was prepared as follows. The carboxyl-dye intermediate (L) (30 mg) and 30mg of N-hydroxysuccinimide (5 equivalents) were dissolved in a mixture of acetonitrile (6 ml) and dimethylformamide (1 ml). Dicyclohexylcarbodiimide (15 mg, 1.5 equivalents) was added and the mixture was stirred at 22° C. for 20 hours. The urea by-product was removed by filtration and washed with acetonitrile (3×2 ml). The combined filtrates were concentrated by rotary evaporation and the dye was precipitated from the remaining DMF by the addition of 20 ml ether. The resulting solid was collected on a sintered glass filter and dried under vacuum. A dark blue powder (30 mg) was obtained. The active ester showed, by TLC, single products when reacted with either methylamine in methanol or taurine in methanol/water.

λ Abs=750 nm (water), $\epsilon_{750}$=150,000 (water), Max
λ Fluor=775 nm (water) Max Example 5

Labeling Antibody with a Reactive Cyanine Dye IV

To 1 mg of sheep anti-mouse-IgG antibody in 250 ul of 0.1M sodium carbonate/bicarbonate (pH 9.2) was added 10 ul of dye solution (4.42 mg/ml DMSO), giving a molar ratio of dye:protein of 10:1. The reaction mixture was stirred at 22° C. for 2 hours, then passed over a Sephadex G-15 desalting column (2.5 ml bed volume), preconditioned with phosphate buffered saline. The dye-conjugated protein obtained from the column had an apparent ratio of about 5 dyes/protein. Other reactive cyanine dyes bearing N-hydroxysuccinimide esters, isothiocyanate, or dichlorotriazine groups were attached to antibody molecules by essentially the same procedure.

Example 6

Staining and Microscopic Visualization of Human Lymphocytes with Cyanine Dye IV Conlucated to Sheep Antimouse IgG Antibody Freshly isolated peripheral lymphocytes were treated at zero degrees for 30 minutes with mouse anti-Beta2-microglobulin (0.25 μg/106 cells). The cells were washed twice with DMEM buffer and were then treated with dye IV-labeled sheep anti-mouse-IgG antibody (1 μg per 106 cells). After a 30 minute incubation at 0° C., the excess antibody was removed and the cells were again washed twice with DMEM buffer. Aliquots of the cells were fixed on slides for analysis by fluorescence microscopy. Under the microscope the stained lymphocytes on the slide were excited with light at 705–740 nm and the fluorescence at 750–805 nm was detected with a COHU red sensitive intensified television camera attached to an image digitizer and television monitor. The cells stained by this method showed fluorescence under the microscope. In a control experiment, use of the primary mouse anti-$B_2$-microglobulin antibody was omitted but the staining and analysis was otherwise carried out as described above. The control sample showed no fluorescence under the microscope indicating that dye IV-labeled sheep anti-mouse antibody does not give significant nonspecific binding to lymphocytes.

Experimental for the Preparation of Cyanine Dye Phosphoramidites for use as 5' Labelling Reagents Example 7

Preparation of 1-Ethyl-2-{5-[1-(5-(2-cyanoethyl-N,N-diisoproylphoshoramidite)pentyl)-3,3-dimethyl-2,3-dihydro-1H-benzo[b]azol-2-yliden]-1,3-pentadienyl}-3,3,-dimethyl-3H-benzo[b]azolium-5-sulfonate 1) 2,3,3-Trimethyl-1-(5-methylcarbonyloxypentyl)-3H-benzo[b]azolium iodide A mixture of 2,3,3-trimethyl-3H-benzo[b]azole (2.39 g, 15 mmol) and 5-iodopentyl acetate (3.84 g, 15 mmol) in 1,2-dichlorobenzene (15 ml) were heated at 120° C. for 6 h and then cooled to ambient temperature. The mixture was then dripped into $Et_2O$ which precipitated the title compound as a red gum which was collected and used without any further purification in subsequent reactions.

ii) 1-Ethyl-2-{5-hydroxypentyl)-3,3-dimethyl-2,3-dihydro-1H-benzo[b]azol-2-yliden-1,3-pentadienyl}-3,3,-dimethyl-3H-benzo[b]azolium-5-sulfonate A mixture of 1-ethyl-2,3,3-trimethyl-3H-benzo[b]azolium-5-sulfonate (267 mg, 1 mmol) and malonaldehyde bis(phenylimine) monohydrochloride (293mg, 1.1 mmol) in AcOH (2.5 ml) and $Ac_2O$ (2.5 ml) were heated at ca. 110° C. for 1.5 h. The reaction mixture was then colled to ambient temperature and concentrated in vacuo. To the residue was added 2,3,3-trimethyl-1-1-(5-methylcarbonyloxypentyl)-3H-benzo[b]azolium iodide (ca 500 mg) as a solution in pyridine (2.5 ml) followed by $Ac_2$) (2.5 ml). the resultant mixture was left stirring at ambient temperature and monitored by UV. The absorption at 450 nm decreased to virtually zero with a corresponding increase in the absorption at 644 nm. The mixture was then concentrated in vacuo, redissolved in dichloromethane, washed with 1 M HCl, saturated $NaHCO_3$, brine, dried over $MgSO_4$ and concentrated in vacuo. The residue was redissolved in MeOH (50 ml) and $K_2CO_3$ (200 mg) was added. After stirring at ambient temperature for 45 min the reaction mixture was concentrated in vacuo to ca.5 ml, diluted with dichloromethane, washed with 1 M HCl, brine, dried over $MgSO_4$ and concentrated in vacuo. The residue was then purified by flash column chromatography, $SiO_2$ dichloromethane-25% MeOH:dichloromethane gradient, to yield the title compound as a dark blue solid (350 mg, 64%) (The product dye was assumed to be the internal salt) $\lambda_{max}$ 644 (MeOH) 644 nm; $\delta_H$ (270 MHz; $CDCl_3/CD_3OD$) 1.31 (3H, t, $CH_2CH_3$), 1.38–1.85 (18H, m), 3.53 (2H, t, $CH_2OH$), 3.87–4.04 (4H, m, $CH_2N$ and $CH_2N$), 6.03 (2H, m, α-vinyl H), 6.45 (1H, t, γ-vinyl H), 6.98–7.11 (2H, m, ArH), 7.17–7.40 (3H, m, ArH) and 7.73–7.95 (4H, m, ArH and 2 β-vinyl H).

iii) 1-Ethyl020{5-[1-(5-(2-cyanoethyl-N,N-diisopropylphosphoromnidite)pentyl)-3,3-dimethyl-2,3-dihydro-1H-benzo[b]azol-2-yliden]1,3-pentadienyl}-3,3,-dimethyl-3H-benzo[b]azolium-5-sulfonate (I)

1-Ethyl-2-{5-[1-(5-hydroxypentyl)-3,3-dimethyl-2,3-dihydro-1H-benzo[b]azol-2-yliden]-1,3-pentadienyl}-3,3,-dimethyl-3H-benzo[b]azolium-5-sulfonate (100 mg) was dried azeotropically with MeCN and then under high vacuum. MeCN (5 ml) was added to the dried dye followed by a solution of 2-cyanothyl-N,N,N',N'-tetraisopropylphosphorodiamidite (ca. 250 mg in MeCN (2 ml)) and then tetrazole (50 μl of a 10 mg/ml solution in MeCN). After a few minutes DMF (1 ml) was added followed by a further aliquot of tetrazole solution (100 μl) after ca. 1 hr. After ca. a further 1 hr the MeCN was removed in vacuo and the crude solution of phosphoramidite was used stored at –70° C. under nitrogen. No purification was attempted and the crude reaction mixture was used in subsequent reactions.

Example 8

Potassium 3-ethyl-2-{5-[3-(5-(2-cyanoethyl-N,N-diisopropylphosphoramidite)pentyl)-1,1-dimethyl-2,3-dihydro-1H-naptho[2,1-bazol-2-yliden]-1,3-pentadienyl}-1,1-dimethyl-1H-naptho[2,1b]azolium-6,8-disulfonate 1) 1,1,2-Trimethyl-3-(5-methylcarbonyloxypentyl)-1H-naptho[2,1b]azolium iodide This prepared is a similar manner to 2,3,3-trimethyl-1-(5-methylcarbonyloxypentyl)-3H-benzo[b]azolium iodide but starting from 1,1,2-trimethyl-1H-naptho[2,1-b]azole and 5-iodopentyl acetate.

ii) Potassium 3-ethyl-2-{5-[3-(5-hydroxypentyl)-1,1-dimethyl-2,3-dihydro-1H-naptho[2,1-bazol-2-yliden]-1,3-pentadienyl}-1,1,-dimethyl-1H-naptho[2,1b]azolium-6, 8-disulfonate A mixture of potassium 3-ethyl-1,1,2-trimethyl-1H-naptho[2,1-b]azolium-6,8-disulfonate (1.08 g) and malonaldehyde bis(phenylimine) monohydrochloride 512 mg) in AcOH(20 ml) was heated at 120° C. for 8 h and then cooled to ambient temperature. 1,1,2-Trimethyl-3-(5-methylcarbonyloxypentyl)-1H-naptho[2,1-b]azolium iodide (835 mg) was added followed by pyridine (20 ml) and $Ac_2O$ (2 ml) and the mixture was allowed to stand at ambient temperature for 16 h before being concentrated in vacuo. The residue was then purified by reversed phase HPLC to afford the title compound as a dark solid, iii) Potassium 3-ethyl-2-{5-[3-(5-(2-cyanoethyl-N,N-diisopropylphosphoramidite)pentyl)-1,1-dimethyl-2,3-dihydro- 1H-naptho[2,1-bazol-2-yliden]-1,3-pentadienyl}-1, 1,-dimethyl-1H-naptho[2,1b]azolium-6,8-disulfonate (II)

To a stirred solution of potassium 3-ethyl-2-{5-[3-(5-hydroxypentyl)-1,1-dimethyl-2,3-dihydro-1H-naptho[2,1-b]azol-2-yliden]-1,3-pentadienyl}-1,1-dimethyl-1H-naptho [2,1]b]azolium-6,8-disulfonate (65 mg) in DMF (2.1 ml) at ambient temperature was added diisopropylethylamine (148 μl, 0.85 mmol) followed by 2-cyanoethyl-N,N'-diisopropylchlorophosphoramidite (100 μl). After 90 min further aliquots of diisopropylethylamine (148 μl) and 2-cyanoethyl-N,N'-diisopropylchlorophosphoramidite (100 μl) were added to the reaction mixture. Stirring was continued for a while and then the reaction vessel was sealed under nitrogen and stored in a –70° C. freezer until use. No purification was attempted and the crude reaction mixture was used in subsequent reactions.

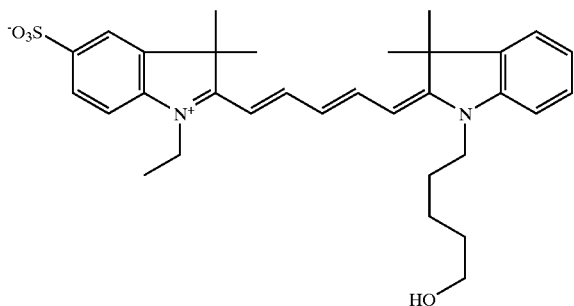

1-Ethyl-2-{5-[1-(5-hydroxypentyl)-3,3-dimethyl-2,3-dihydro-1H-benzo[b]azol-2-yliden]-1,3-pentadienyl}-3,3,-dimethyl-3H-benzo[b]azolium-5-sulfonate

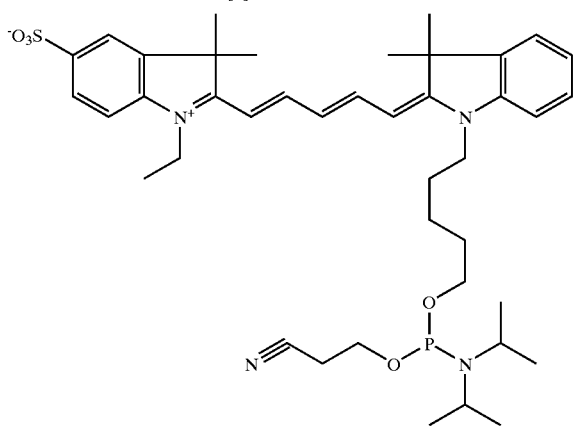

1-Ethyl-2-{5-[1-(5-(2-cyanoethyl-N,N-diisopropylphosphoramidite)-pentyl)-3,3-dimethyl-2,3-dihydro-1H-benzo[b]azol-2-yliden]-1,3-pentadienyl}-3,3,-dimethyl-3H-benzo[b]azolium-5-sulfonate (Example I)

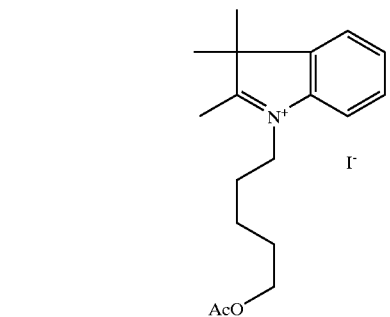

2,3,3-Trimethyl-1-(5-methylcarbonyloxypentyl)-3H-benzo[b]azolium iodide

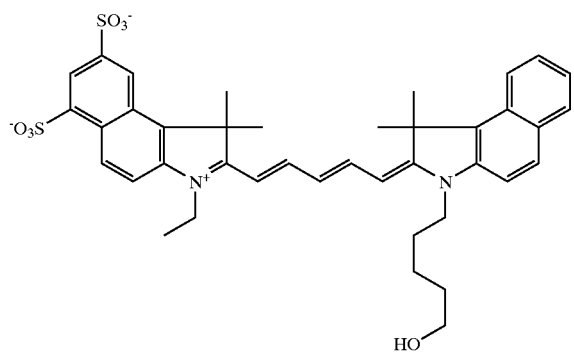

Potassium 3-ethyl-2-{5-[3-(5-hydroxypentyl)-1,1-dimethyl-2,3-dihydro-1H-naptho[2,1-b]azol-2-yliden]-1,3-pentadienyl}-1,1-dimethyl-1H-naptho[2,1-b]azolium-6,8-disulfonate

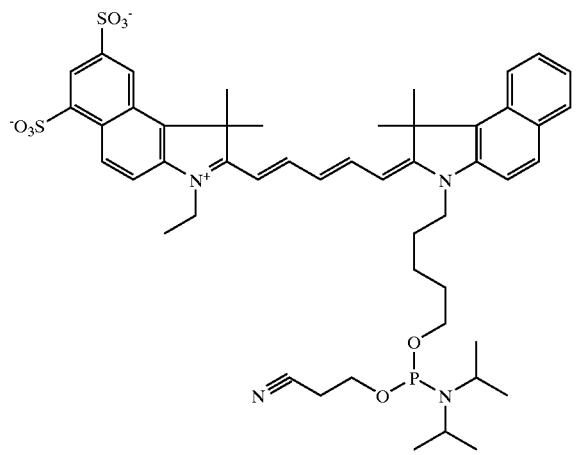

Potassium 3-ethyl-2-{5-[3-(5-(2-cyanoethyl-N,N-diisopropylphosphoramidite)pentyl)-1,1-dimethyl-2,3-dihydro-1H-naptho[2,1-b]azol-2-yliden]-1,3-pentadienyl}-1,1-dimethyl-1H-naptho[2,1-b]azolium-6,8-disulfonate (Example II)

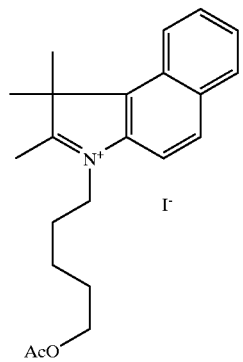

1,1,2-Trimethyl-3-(5-methylcarbonyloxypentyl)-1H-naptho[2,1-b]azolium iodide

Synthesis of Oligonucleotide Primers Labelled at the 5' Terminus with Example 7 or Example 8

Materials

Example 7, 100 mg/ml in dimethylformamide.
Example 8, 65 mg/ml in dimethylformamide.
ABI394 reagent kit for β-cyanoethyl phosphoramidite chemistry, P/N 400852X.
ABI cpg T synthesis columns, 0.2 μmol.
Glen Research iPr-Pac-dG-CE phosphoramidite.
Glen Research dT-CE phosphoramidite.
Glen Research Ac-dC-CE phosphoramidite.
Glen Research Pac-dA-CE phosphoramidite.
50 mM Potassium carbonate in methanol.
Amersham International cyanine reference dyes referred to as Cy5 and Cy5.5.

DNA Synthesis.

An ABI394 instrument was programmed to synthesize the sequence . . .

5'-5tgtaaaacgacggccagt-3'

The sequence is an 18 base universal [−21] M13 forward primer. The 0.2 μmol CE standard cycle was used. Dye phosphoramidites were located at bottle position #5. The end cycle was set to Trityl-On and Manual cleavage/deprotection.

An interrupt was programmed to halt synthesis at the start of the dye coupling cycle to allow manual control of reagent delivery. Three consecutive deliveries of tetrazole+dye-phosphoramidite were used, each with a coupling time of 200 seconds. This was followed by the standard capping and iodine oxidation reactions. The final acetonitrile wash was extended to 60 seconds to flush residual dye from the column.

Cleavage from the Column and Base Deprotection.

The column was opened and the resin put into a 1.5 ml Sarstedt tube. 1 ml of deprotection reagent [50 mM potassium carbonate in methanol] was added. The tube was capped, wrapped in foil to exclude light and gently mixed for 2 hours at ambient temperature [~20° C.].

The tube was uncapped and centrifuged under vacuum in a Speedvac for 15 minutes until the volume reduced to about 0.5 ml. The DNA solution was removed to a fresh tube leaving the CPG support resin behind. The volume was measured and DNA precipitated by addition of 1 M $MgCl_2$ to 20 mM final concentration and 2.5 aqueous volumes of absolute ethanol. After 10 minutes on ice in the dark the DNA was pelleted by centrifugation at 13000 xg for 5 minutes.

The DNA pellet was re-dissolved in 0.1 ml TE pH8.0 and re-precipitated as above.

Finally the DNA was taken up in 0.2 ml TE pH8.0 for determining the absorption spectrum and for HPLC purification.

OD Spectrum 0.1 lml of a 1:200 dilution of the crude dye-primer was scanned between 215–750 nm in a Philips PUV8700 UV/Visible spectrophotometer. DNA concentration and approximate % labelling were calculated prior to HPLC purification.

Example 7 gave a OD260/647 ratio of 1.04, equivalent to ~75% labelled DNA based upon an $\epsilon_m$ of 220000 $M^{-1}$ $cm^{-1}$ for Cy5.

Example 8 gave a OD260/681 ratio of 6.87, equivalent to ~13% labelled DNA using an $\epsilon_m$ of 190000 $M^{-1}$ $cm^{-1}$ fr Cy5. FIGS. 1(a) and (b) show absorbance scans of the oligonucleotide synthesis products after deprotection and ethanol precipitation of the DNA but before HPLC purification.

HPLC Purification

Dye-primers were separated on a 24×0.4 cm Spherisorb ODS-2 $C_{18}$ column using a Varian Vista 5500 system. The program used was as follows:

| Time | % Buffer A | % Buffer B | Flow rate |
|------|-----------|-----------|-----------|
| 0 | 95 | 5 | 1 ml/min |
| 5 | 95 | 5 | " |
| 50 | 90 | 50 | " |
| 60 | 30 | 70 | " |
| 70 | 30 | 70 | " |
| 80 | 95 | 5 | " |
| 90 | 95 | 5 | " |
| 91 | | | 0 |

Buffer A = 0.1 M ammonium acetate
Buffer B = acetonitrile

Column eluate was monitored at 260 nm and either 650 nm or 680 nm.

Figure 2:
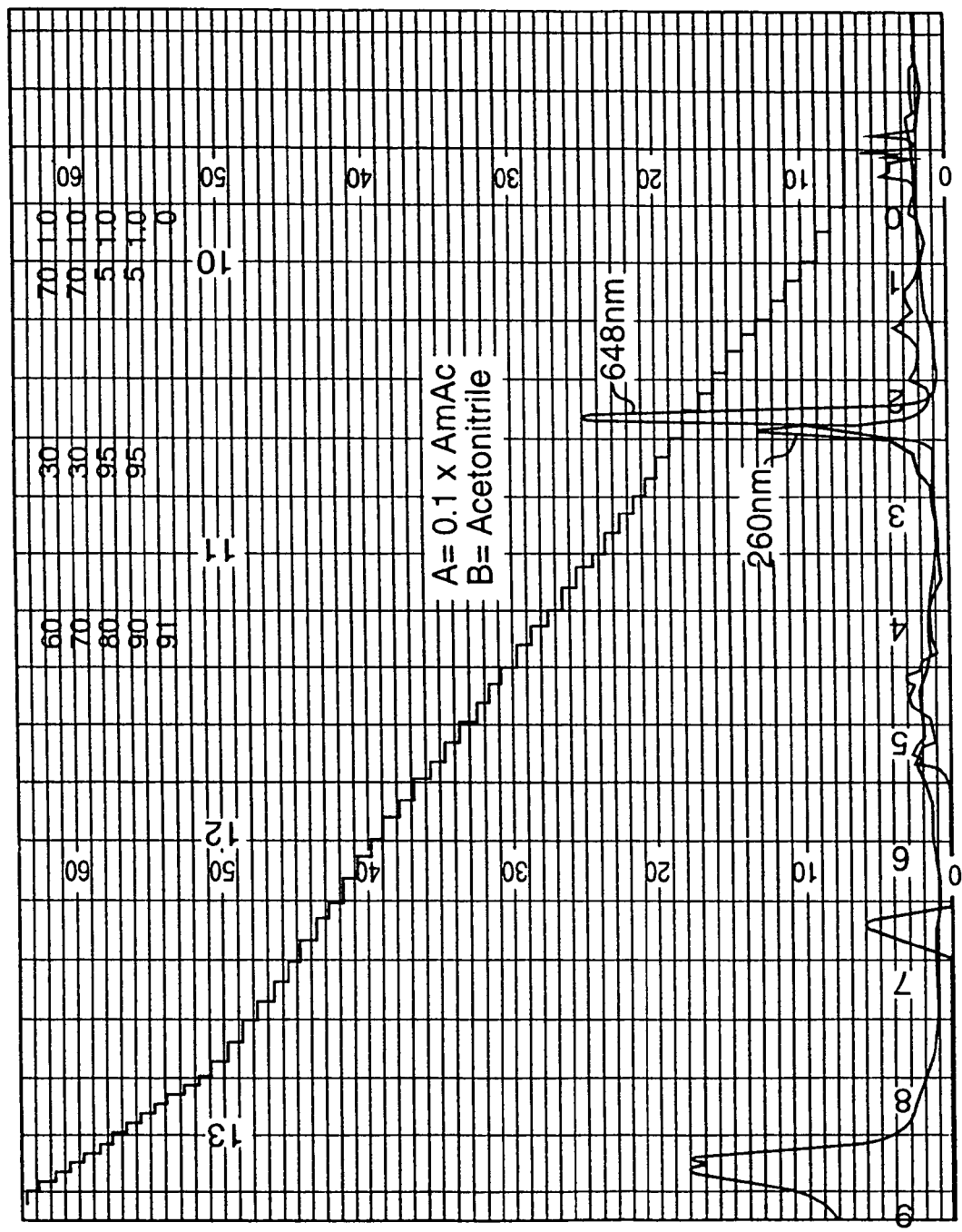
FIG. 2 is an HPLC trace showing separation of the labelled oligonucleotide from unlabelled DNA and free dye of Example 7.

Dye primers eluted at approximately 20% acetonitrile. The HPLC trace for Example 7 is shown in FIG. 2. The two lines record dye absorbance at 648 nm [tallest peak] and DNA at 260 nm. Increasing acetonitrile concentration is indicated by the diagonal line. There is a small amount of unlabelled DNA eluting around 10% acetonitrile and some free dye eluting late in the run [far left]. The major product is a single peak of dye-primer exhibiting absorbance at both wavelengths.

Figure 3A:
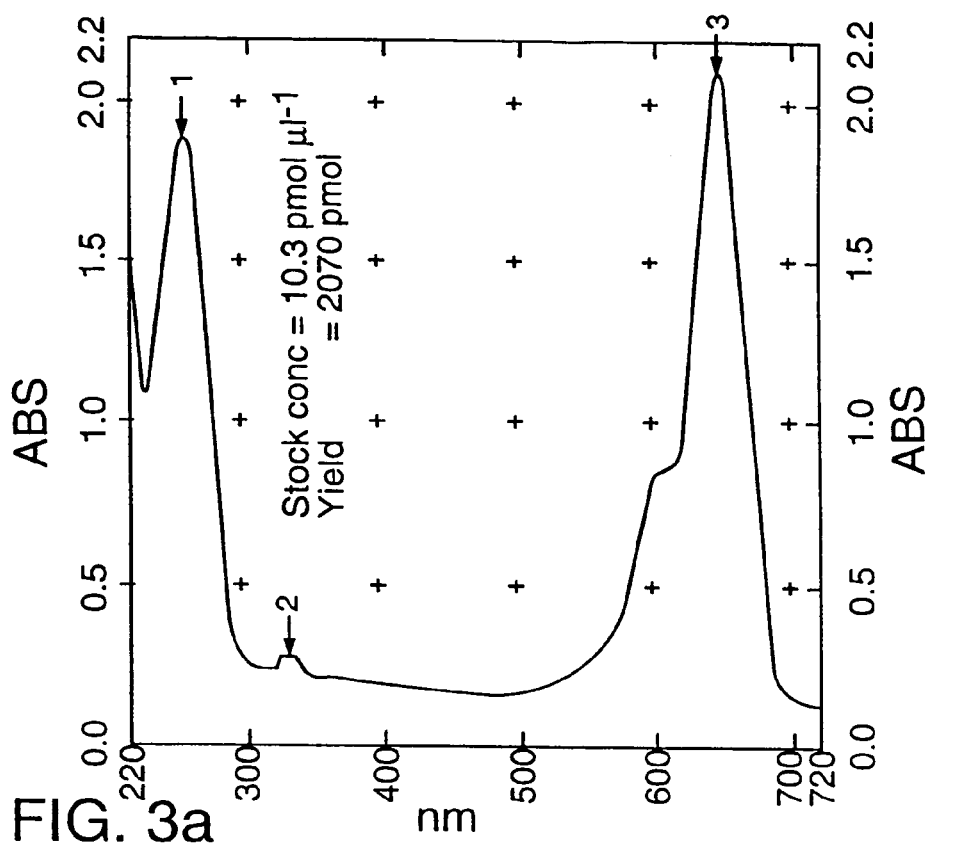
FIGS. 3(a) and (b) are the absorbance scans of the dye primers of Examples 7 and 8 after HPC purification.
Figure 3B:
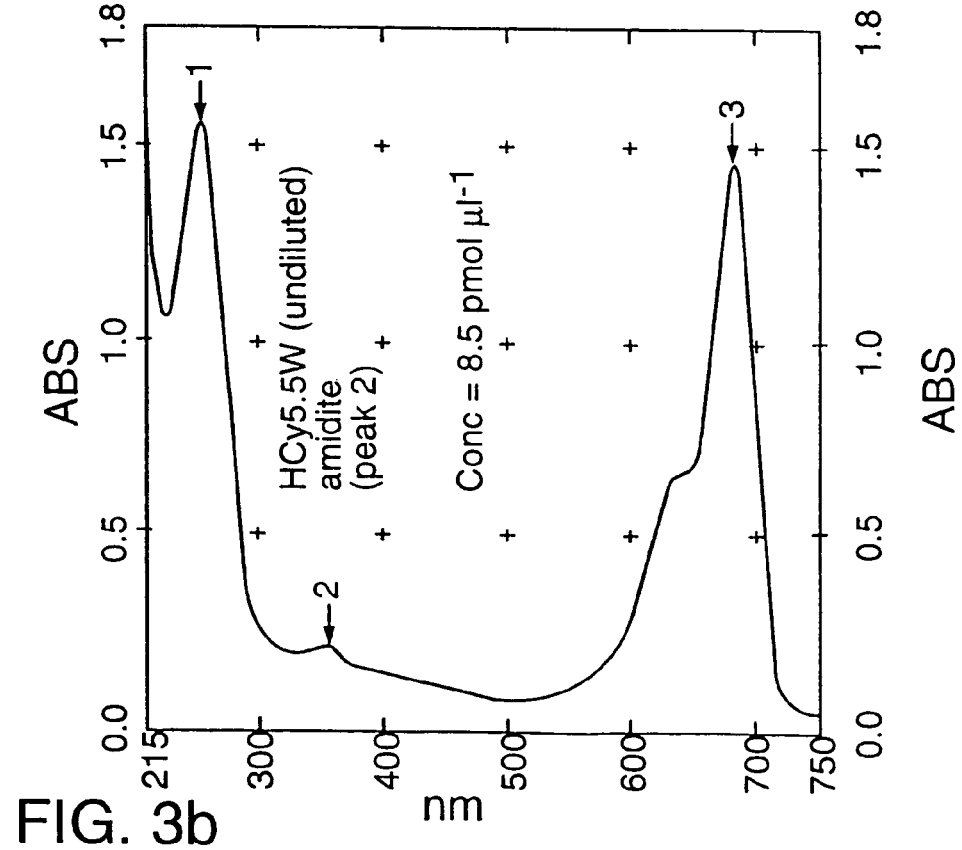

Dye-Primer containing HPLC fractions were evaporated to dryness in a Speedvac, re-dissolved in 0.1 ml TE buffer and ethanol precipitated [as described earlier] to remove salt. A second OD spectrum was taken to determine the primer concentration prior to DNA sequencing. See FIG. 3.

DNA Sequencing Reactions

Primers were diluted in TE buffer to 2 pmol/$\mu$l and used to sequence bacteriophage M13 mp8 single stranded DNA using a cycle sequencing kit RPN2444 provided by Amersham International's ThermoSequenase. Briefly, 2 pmol of fluorescent primer was mixed with 0.4 pmol of DNA template and made up to 20 $\mu$l with sterile deionised water. The mixture was split into 4 equal aliquots designated A,C,G and T. Next 2 $\mu$l of A,C,G or T reagent [containing ThermoSequenase DNA polymerase, reaction buffer and nucleotides] was added to the appropriate tube which was then capped and transferred to a Perkin-Elmer 9600 thermal cycler. The thermocycler program consisted of denaturation at 95° C. for 30 seconds followed by annealing and polymerisation at 60° C. for 30 seconds and was repeated 25 times. After cycling, 3 $\mu$l of formamide loading buffer was added and the samples were evaporated under vacuum in a SpeedVac for 10 minutes to reduce the volume to ~3 $\mu$l. The samples were then loaded on to a 6% HydroLink Long Ranger gel containing 6M urea and 1.2× TBE buffer and electrophoresed at 1500V for 10 hours. Two different automated fluorescent DNA sequences were used. For Example 7, a modified Vistra DNA Sequencer 725 with a 10 mW 633 nm Helium-Neon laser and 650 nm interference filter set and for Example 8, a prototype Hitachi SQ-Y1 instrument with a 3 mW 650 nm laser diode and 680 nm color glass filter. Examples of the analysed data are shown in FIG. 4.

Figure 4A:
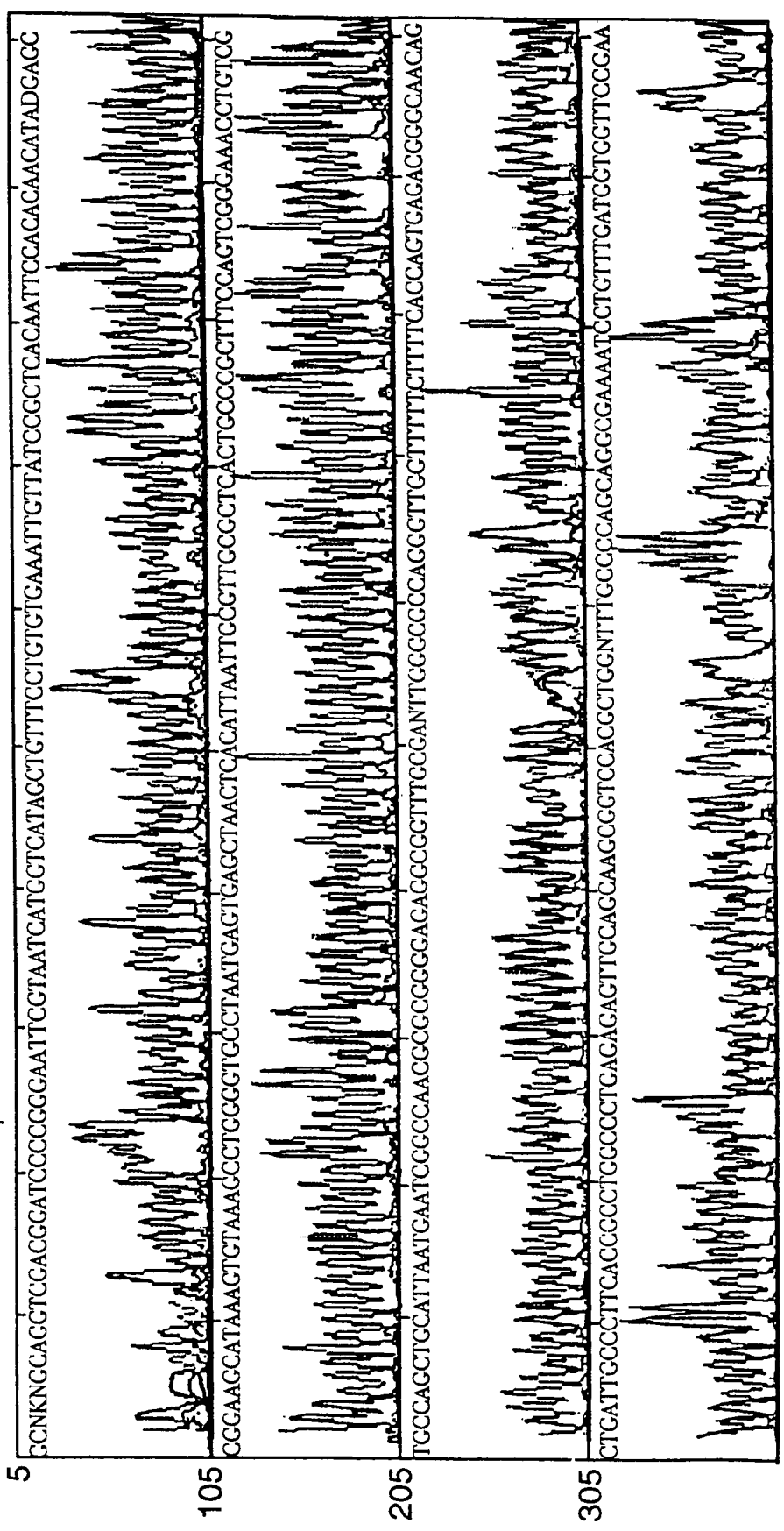
FIGS. 4(a) and (b) are DNA sequence traces for the dye primers of Examples 7 and 8.
Figure 4B:
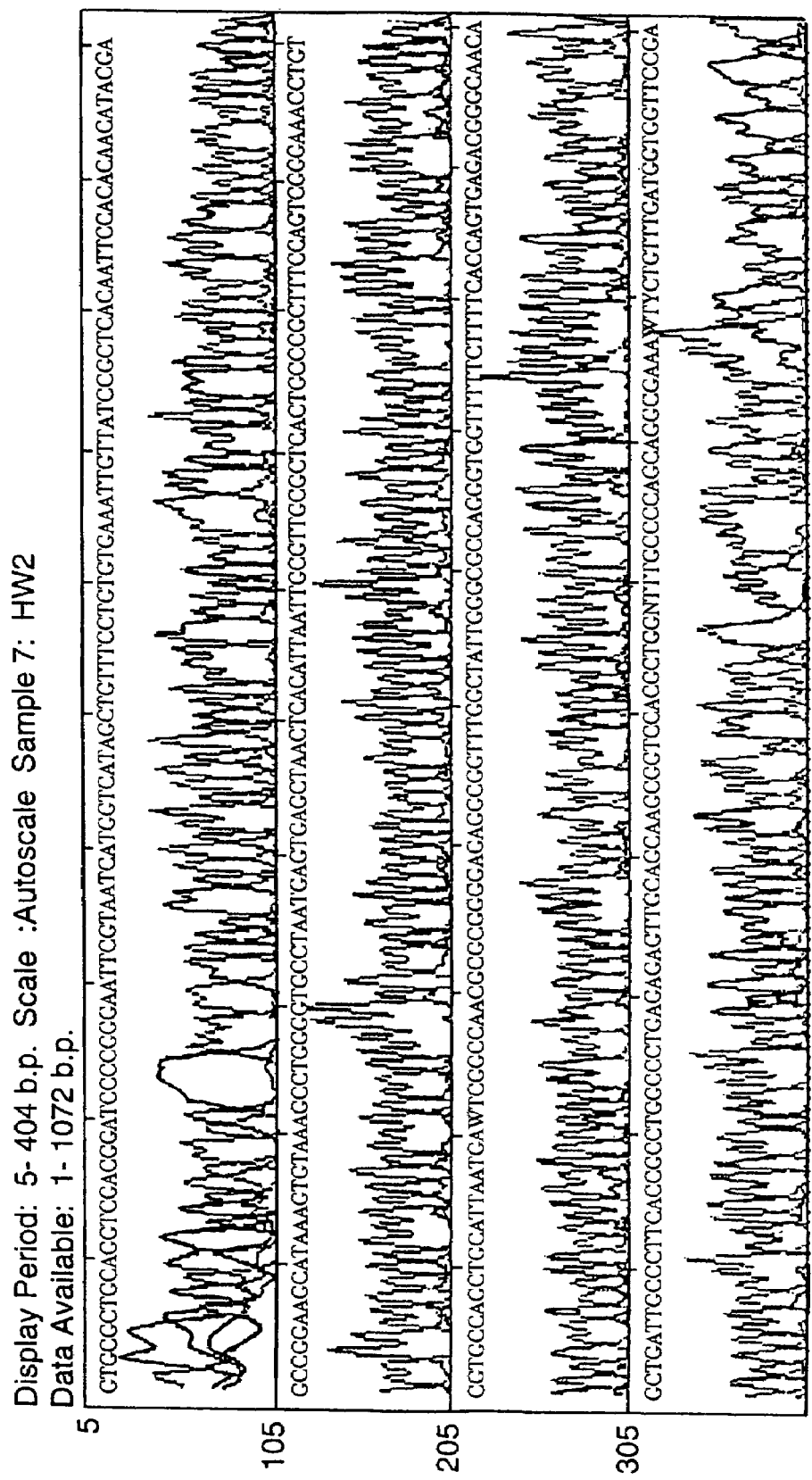

FIG. 4(a) Sequence data for the dye-primer of Example 7 was prepared from from a red-laser version of the Vistra DNA Sequencer 725 instrument. The first 400 bases are shown from a total of 660 bases called by V2.01 analysis software.

FIG. (4b) Sequence data for the dye-primer of Example 8 was prepared on a Hitachi SQ-Y1 automated fluorescent DNA sequencer. The first 400 bases are shown out of 1072 bases called by V1-0 analysis software.

The detection limit of both dye primers in fluorescent sequencing applications was in the attomole range per DNA band, comparable that of Texas Red primers normally used on the Vistra DNA sequencer 725.

Band resolution and sequence accuracy were good, typically >98.0% accuracy for 600 bases.

I claim:

1. A method for labeling a component of an aqueous liquid comprising:
    a) adding to said liquid containing said component a luminescent dye selected from the group consisting of cyanine, merocyanine and styryl dyes containing at least one sulphonate or sulphonic acid attached to an aromatic nucleus which dye is reactive with said component;
    b) reacting said dye with said component so that said dye labels said component; and
    wherein said dye has a molar extinction coefficient of at least 50,000 liters per mole centimeter, a quantum yield of at least 5 percent and absorbs and emits maximally in the 400 to 900 nm range.

2. The method according to claim 1 wherein said component is selected from antibodies, proteins, peptides, enzyme substrates, hormones, lymphokines, metabolites, receptors, antigens, haptens, lectins, toxins, carbohydrates, sugars, oligosaccharides, polysaccharides, nucleotides, derivatised nucleotides, nucleic acids, deoxynucleic acids, derivatised nucleic acids, derivatised deoxynucleic acids, DNA fragments, RNA fragments, derivatised DNA fragments, derivatised RNA fragments and drugs.

* * * * *